(12) United States Patent
Rabito et al.

(10) Patent No.: US 12,318,287 B2
(45) Date of Patent: Jun. 3, 2025

(54) PROSTHETIC HEART VALVE, SYSTEMS, AND METHODS

(71) Applicant: Magnolia Medical Corp., Newport Beach, CA (US)

(72) Inventors: Glen Rabito, Lake Forest, CA (US); Hieu Luong, Westminster, CA (US); Robert C. Taft, Orange, CA (US)

(73) Assignee: Magnolia Medical Corp., Newport Beach, CA (US)

(*) Notice: Subject to any disclaimer, the term of this patent is extended or adjusted under 35 U.S.C. 154(b) by 0 days.

(21) Appl. No.: 18/812,932

(22) Filed: Aug. 22, 2024

(65) Prior Publication Data

US 2024/0407919 A1 Dec. 12, 2024

Related U.S. Application Data

(63) Continuation of application No. PCT/US2023/066708, filed on May 5, 2023.

(60) Provisional application No. 63/383,335, filed on Nov. 11, 2022, provisional application No. 63/366,001, filed on Jun. 7, 2022, provisional application No. 63/364,248, filed on May 5, 2022.

(51) Int. Cl.
*A61F 2/24* (2006.01)

(52) U.S. Cl.
CPC .... *A61F 2/2418* (2013.01); *A61F 2220/0008* (2013.01)

(58) Field of Classification Search
CPC .................................................. A61F 2/2418
See application file for complete search history.

(56) References Cited

U.S. PATENT DOCUMENTS

| 10,052,201 B2 | 8/2018 | Zhang et al. |
| 10,543,079 B2 | 1/2020 | Quill et al. |
| 10,624,736 B2 | 4/2020 | Keidar |
| 11,872,131 B2 | 1/2024 | Hariton et al. |
| 2013/0310928 A1 | 11/2013 | Morriss et al. |

(Continued)

FOREIGN PATENT DOCUMENTS

| CN | 111163727 A | 5/2020 |
| EP | 2777617 A1 | 9/2014 |

OTHER PUBLICATIONS

WIPO, U.S. International Search Authority, International Search Report and Written Opinion mailed Jan. 4, 2024 in International Patent Application No. PCT/US2023/066708, 14 pages.

(Continued)

*Primary Examiner* — Suba Ganesan
(74) *Attorney, Agent, or Firm* — Inskeep IP Group, Inc.

(57) ABSTRACT

Prosthetic valve support structures of this specification include a body portion, an atrial flange portion, and a leaflet engaging portion. As the support structure (and the valve as a whole) is pushed out of or otherwise unrestrained from a delivery device, the free end(s) of the leaflet engaging portion will begin to bend radially outward or away from the body portion and will continue bending as more is exposed until its free end(s) are angled in an inflow direction, thereby positioning themselves between the radial outside of the native valve leaflets and the outflow track beyond the native valve annulus. As the support structure fully expands, the native valve leaflets remain trapped or engaged between the leaflet engaging portion and the body portion.

20 Claims, 23 Drawing Sheets

(56) References Cited

U.S. PATENT DOCUMENTS

| | | |
|---|---|---|
| 2014/0379074 A1 | 12/2014 | Spence et al. |
| 2016/0158000 A1 | 6/2016 | Granada et al. |
| 2017/0056166 A1* | 3/2017 | Ratz ................. A61F 2/2418 |
| 2017/0065409 A1 | 3/2017 | Scorsin et al. |
| 2017/0100236 A1* | 4/2017 | Robertson ........... A61F 2/2418 |
| 2019/0015202 A1 | 1/2019 | Hacohen |
| 2019/0262129 A1* | 8/2019 | Cooper ............. A61F 2/2427 |
| 2019/0336287 A1 | 11/2019 | Montorfano et al. |
| 2022/0006850 A1 | 1/2022 | Cooper et al. |
| 2022/0087816 A1* | 3/2022 | Ratz ................. A61F 2/2418 |
| 2022/0104940 A1 | 4/2022 | Peterson et al. |
| 2022/0175523 A1 | 6/2022 | Dibie et al. |
| 2023/0014100 A1 | 1/2023 | Quadri et al. |
| 2023/0277309 A1 | 9/2023 | Cooper et al. |
| 2023/0363902 A1 | 11/2023 | Hariton et al. |
| 2024/0081981 A1 | 3/2024 | Tayeb et al. |
| 2024/0081986 A1 | 3/2024 | Oba et al. |
| 2024/0173122 A1 | 5/2024 | Chau et al. |
| 2024/0315835 A1 | 9/2024 | Oba et al. |
| 2024/0350260 A1 | 10/2024 | Lv et al. |

OTHER PUBLICATIONS

WIPO, U.S. International Search Authority, Republished International Search Report and Written Opinion mailed Jan. 4, 2024 in International Patent Application No. PCT/US2023/066708, 5 pages.

\* cited by examiner

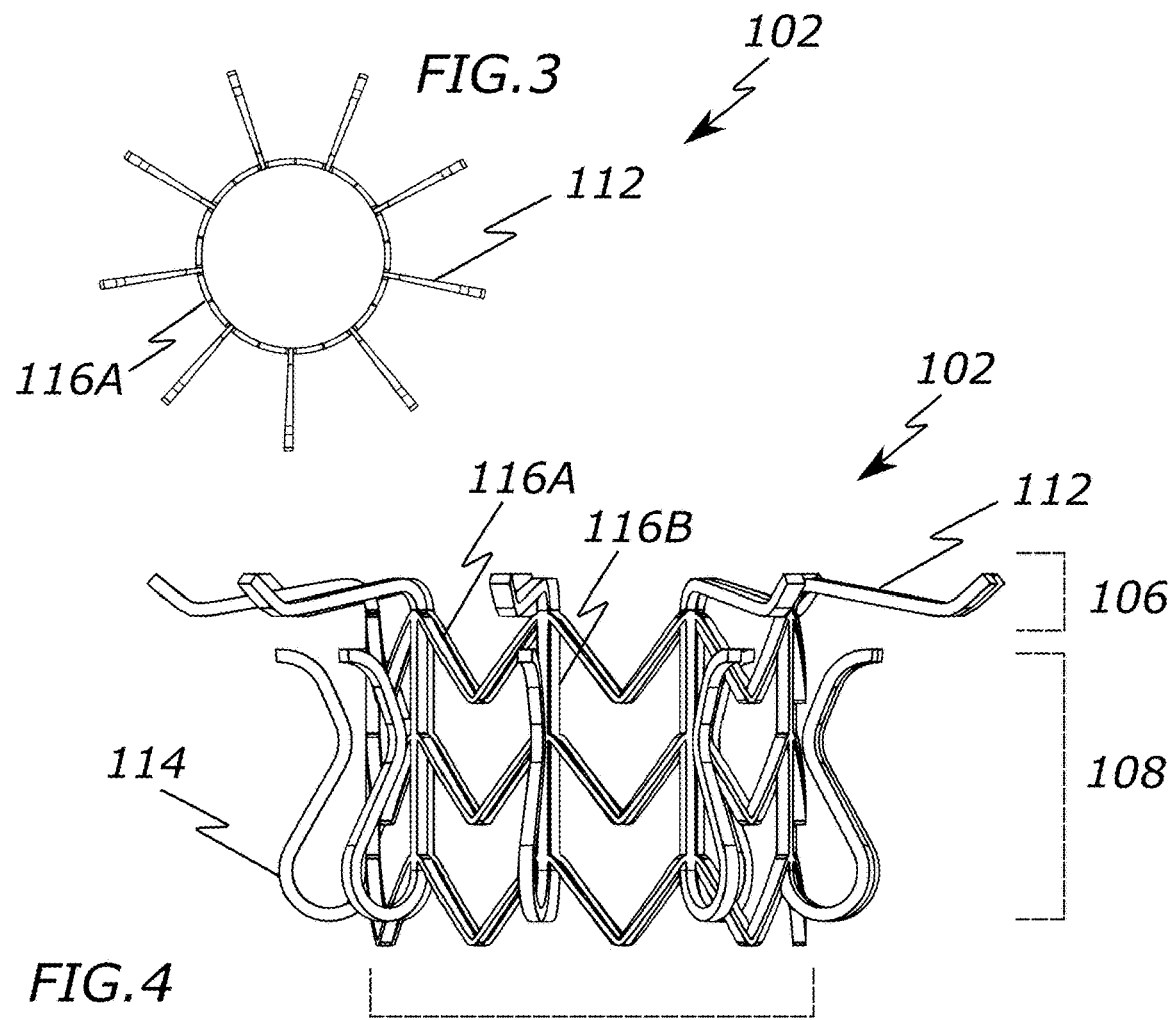
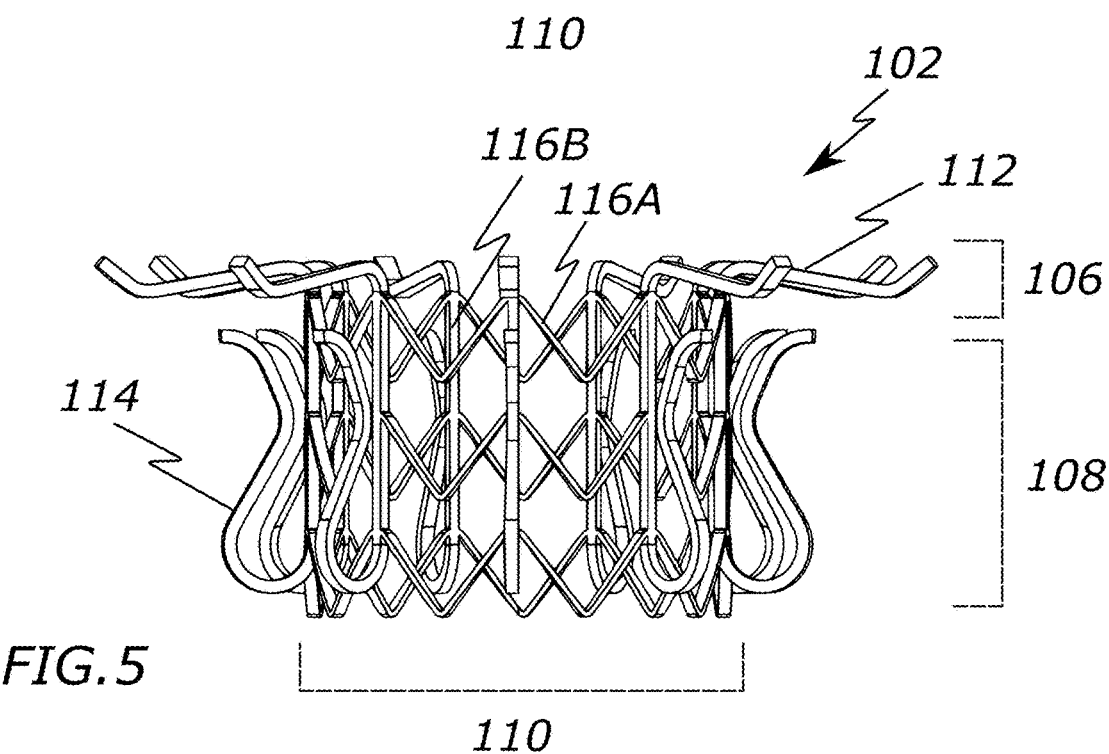

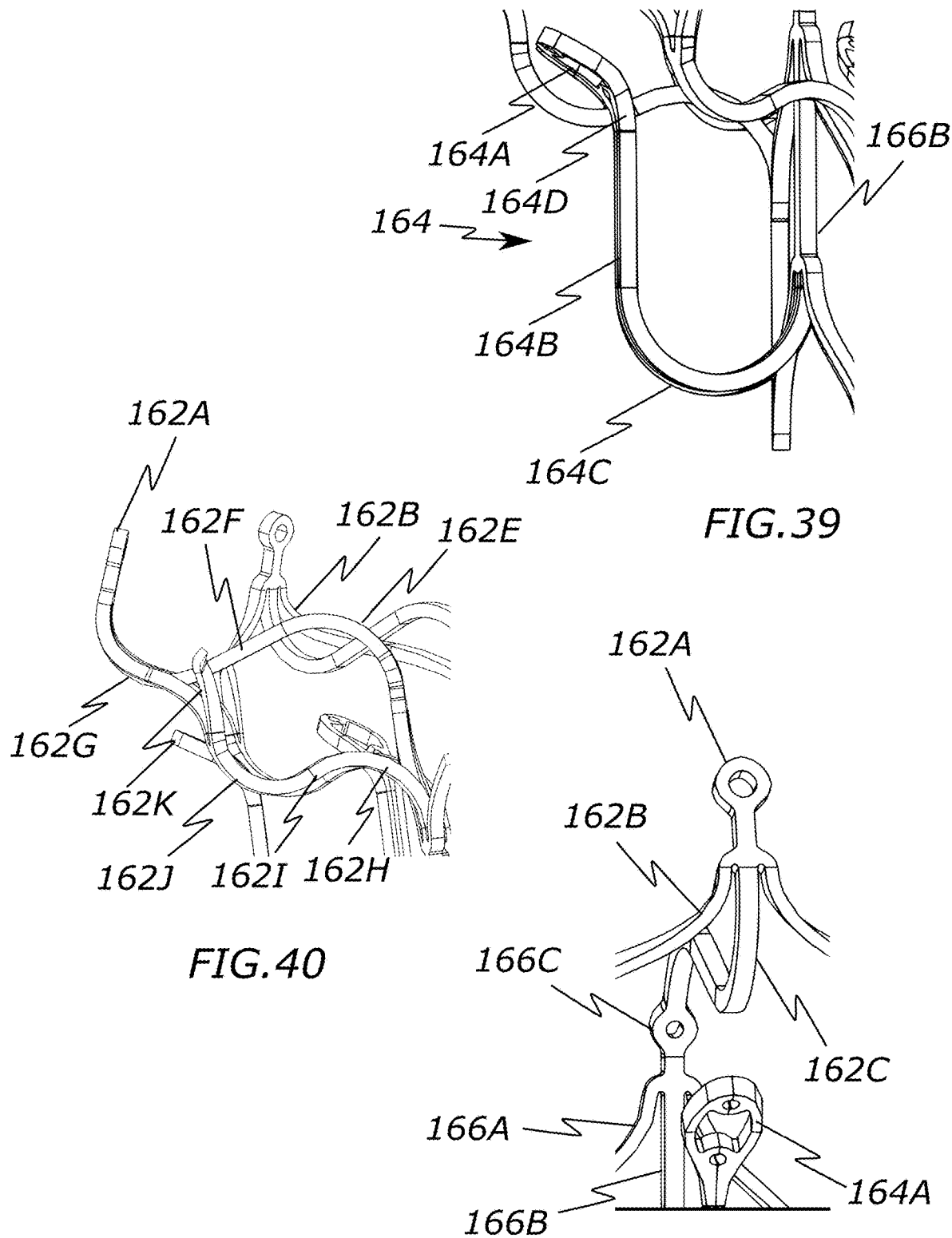

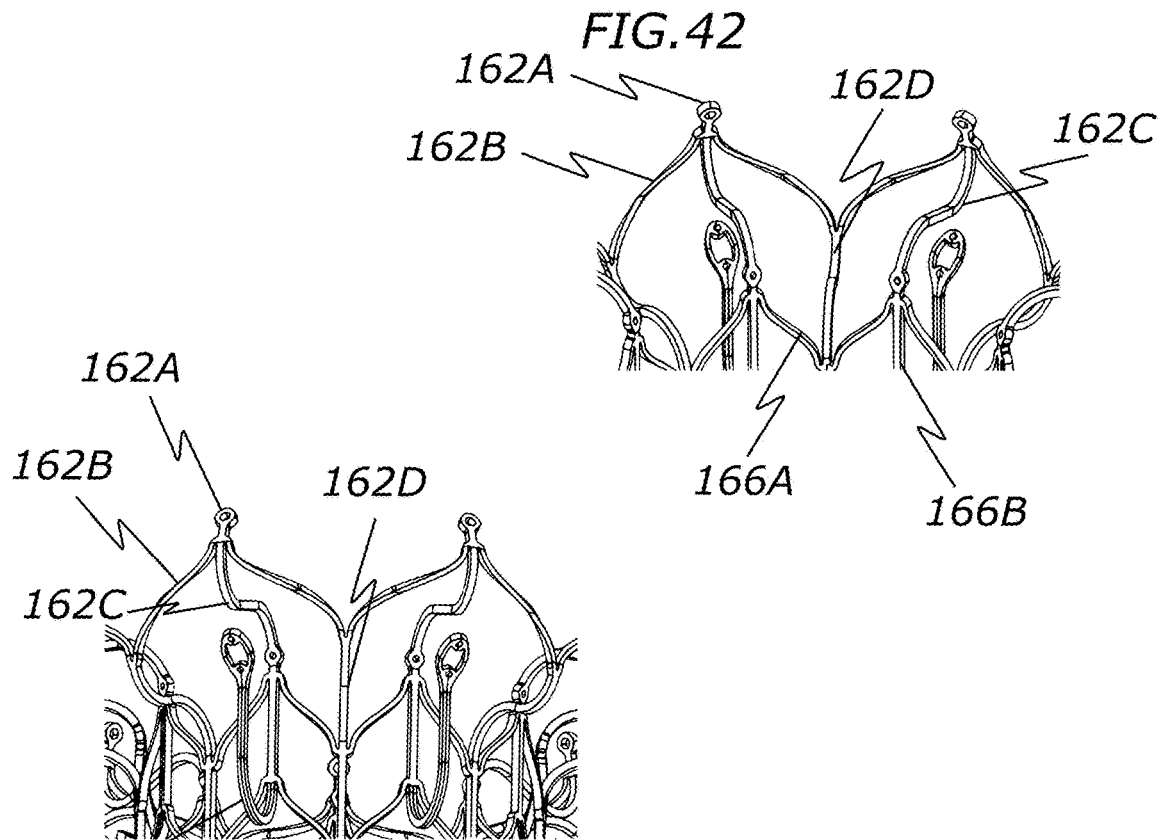
FIG.42
FIG.43
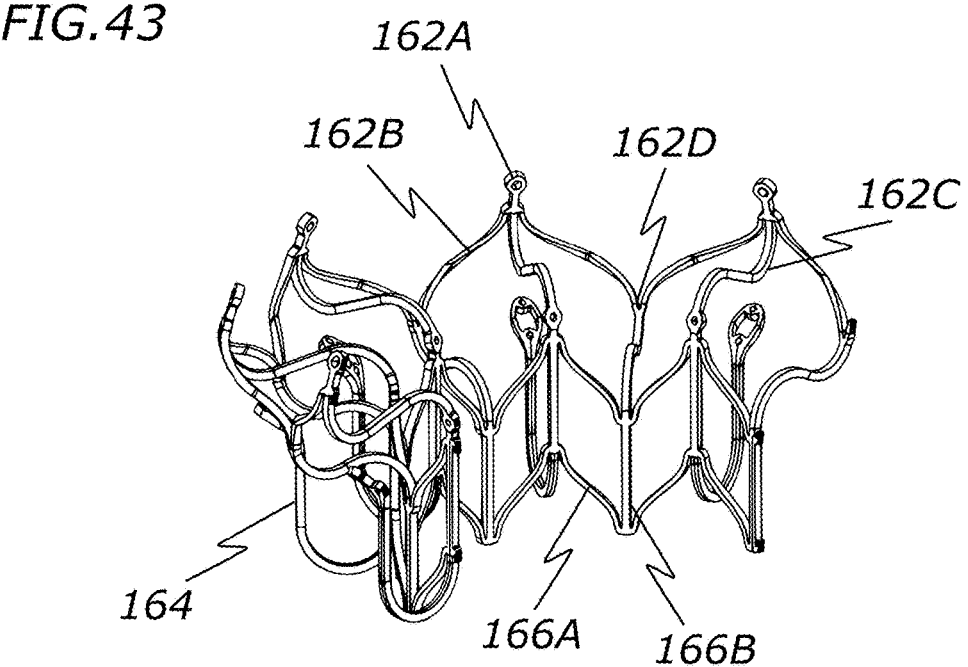
FIG.44

PROSTHETIC HEART VALVE, SYSTEMS, AND METHODS

RELATED APPLICATIONS

This application is a continuation and claims priority to International Application PCT/US2023/066708 filed May 5, 2023, entitled Prosthetic Heart Valve, Systems, And Methods, which claims benefit of and priority to U.S. Provisional Application Ser. No. 63/364,248 filed May 5, 2022 entitled Valve and Valve Docking System, U.S. Provisional Application Ser. No. 63/366,001 filed Jun. 7, 2022 entitled Heart Valve and Valve Docking System, and U.S. Provisional Application Ser. No. 63/383,335 filed Nov. 11, 2022 entitled Valve and Valve Docking System, all of which are hereby incorporated herein by reference in their entireties.

BACKGROUND OF THE INVENTION

Heart valve disease is a common condition affecting millions of people worldwide. The heart has four valves, which regulate blood flow by opening and closing during each heartbeat. When these valves become damaged or diseased, they may not function properly, leading to a variety of symptoms such as shortness of breath, fatigue, and chest pain. In severe cases, heart valve disease can lead to heart failure or even death.

Traditional treatment for heart valve disease involves surgical replacement of the affected valve with a prosthetic valve. While this procedure is effective, it is invasive and requires a significant recovery period. Additionally, some patients may not be eligible for surgery due to other health conditions.

In recent years, there has been growing interest in minimally invasive techniques for heart valve replacement, such as Transcatheter Aortic Valve Replacement (TAVR). This technique involves inserting a collapsible valve into the heart through a catheter, typically inserted into the femoral artery. The valve is then deployed within the damaged valve, replacing it and restoring normal blood flow.

More recently, there has been a growing interest in using this technique for the replacement of the mitral and tricuspid valves, known as Transcatheter Mitral Valve Replacement (TMVR) and Transcatheter Tricuspid Valve Replacement (TTVR), respectively. These valves are more complex than the aortic valve, and their replacement using traditional surgical techniques can be challenging. TMVR and TTVR offer a less invasive option for patients with mitral or tricuspid valve disease, who may not be eligible for traditional surgical valve replacement.

TMVR and TTVR require specialized devices, which are designed to fit within the unique shape of the mitral or tricuspid valve. These devices are typically made of biocompatible materials and are designed to be deployed through a catheter, similar to the TAVR procedure.

Overall, TMVR and TTVR offer a promising new option for patients with mitral or tricuspid valve disease, who may not be eligible for traditional surgical valve replacement. As with any new medical technology, there are still many challenges to be addressed, including device design, patient selection, and long-term outcomes. However, the potential benefits of these techniques make them an exciting area of research and development in the field of cardiology.

SUMMARY OF THE INVENTION

Prosthetic valve support structures of this specification include a body portion, an atrial flange portion, and a leaflet engaging portion. As the support structure (and the valve as a whole) is pushed out of or otherwise unrestrained from a delivery device, the free end(s) of the leaflet engaging portion will begin to bend radially outward or away from the body portion and will continue bending as more is exposed until its free end(s) are angled in an inflow direction, thereby positioning themselves between the radial outside of the native valve leaflets and the outflow track beyond the native valve annulus. As the support structure fully expands, the native valve leaflets remain trapped or engaged between the leaflet engaging portion and the body portion.

In some aspects, the techniques described herein relate to a prosthetic heart valve, including: a body portion having a generally cylindrical shape; an atrial flange portion extending radially outward from an inflow end of the body portion and forming a plurality of petal shapes annularly around the body portion; and, a leaflet engaging portion including a plurality of engagement struts connected at an outflow end of the body portion and extending in an inflow direction along an outside of the body portion.

In some aspects, the techniques described herein relate to a prosthetic heart valve, wherein the body portion includes a plurality of elongated vertical body struts that alternate in axial positions relative to each other.

In some aspects, the techniques described herein relate to a prosthetic heart valve, wherein the body portion includes a plurality of horizontal body struts forming a "V" shape or angle and that are each connected to two of the plurality of vertical body struts.

In some aspects, the techniques described herein relate to a prosthetic heart valve, wherein the body portion has a length within an inclusive range of about 14 mm to about 18 mm, and has a radius within an inclusive range of about 27 mm to about 30 mm.

In some aspects, the techniques described herein relate to a prosthetic heart valve, wherein the atrial flange portion includes a plurality of upper radial flange struts and a plurality of lower radial flange struts that each extend from the body portion; wherein the upper radial flange struts are positioned further toward an inflow end of the prosthetic heart valve than the lower radial flange struts.

In some aspects, the techniques described herein relate to a prosthetic heart valve, wherein the atrial flange portion includes a plurality of radial flange struts; wherein the upper portion of the radial flange struts are connected to the atrial flange portion and the lower portion of the radial flange struts are not connected to the atrial flange portion and angled toward an outflow end of the prosthetic heart valve.

In some aspects, the techniques described herein relate to a prosthetic heart valve, wherein the plurality of upper radial flange struts and the plurality of lower radial flange struts each have: a first angle within an inclusive range of about 90 degrees and 130 degrees, a relative straight portion with a length within an inclusive range of about 3 mm and about 10 mm, a second angle within an inclusive range of about 20 degrees and about 150 degrees, and a terminal portion with a length within an inclusive range of about 1 mm and 7 mm.

In some aspects, the techniques described herein relate to a prosthetic heart valve, wherein outer ends of the plurality of upper radial flange struts and the plurality of lower radial flange struts are connected to each other via one of a plurality of circumferential radial struts that form petal shapes that accommodate a position difference between the plurality of upper radial flange struts and the plurality of lower radial flange struts.

In some aspects, the techniques described herein relate to a prosthetic heart valve, wherein the plurality of engagement struts form a first curve which curves around to about 180 degrees, a first straight portion with a length within an inclusive range of about 3 mm and about 10 mm, a second curve curving in an opposite direction of curve within an inclusive range of about 90 degrees to about 150 degrees, a rounded portion with a length within an inclusive range of about 2 mm to about 10 mm.

In some aspects, the techniques described herein relate to a prosthetic heart valve, wherein an end region of the plurality of engagement struts are positioned axially between the plurality of lower radial flange struts and the plurality of lower radial flange struts.

In some aspects, the techniques described herein relate to a prosthetic heart valve, wherein the end region of the plurality of engagement struts are positioned to axially overlap the plurality of lower radial flange struts at radially adjacent position within an inclusive range of about 0.1 mm and about 10 mm.

In some aspects, the techniques described herein relate to a prosthetic heart valve, further including a material covering disposed over a framework, wherein the material covering forms one or more triangular gaps along an inflow edge of the body portion.

In some aspects, the techniques described herein relate to a prosthetic heart valve, including: a valve framework having an expanded configuration including: a cylindrical body portion, a plurality of radial struts extending radially from a first end of the cylindrical body portion; and, a plurality of engagement struts connected near a second end of the cylindrical body portion and positioned along an outer side of the cylindrical body portion extending toward the first end; wherein end regions of the plurality of engagement struts extend beyond at least some of the plurality of radial struts.

In some aspects, the techniques described herein relate to a prosthetic heart valve, including: a valve framework having a cylindrical body portion and a leaflet engaging portion connected at a distal region of the body portion; wherein the leaflet engaging portion includes a plurality of engagement struts that extend distally from the body portion when the framework is in a compressed configuration within a delivery device and wherein the plurality of engagement struts bend proximally backward along an outside of the body portion when the framework is in an expanded configuration.

In some aspects, the techniques described herein relate to a prosthetic heart valve, wherein the valve framework further includes a plurality of radial struts extending radially out from a proximal region of the body portion.

In some aspects, the techniques described herein relate to a prosthetic heart valve, wherein end regions of the plurality of engagement struts are positioned proximally beyond some of the plurality of radial struts.

In some aspects, the techniques described herein relate to a prosthetic heart valve, wherein the plurality of radial struts include a first set of radial struts and a second set of radial struts, wherein the first set of radial struts are positioned proximally of the second set of radial struts.

In some aspects, the techniques described herein relate to a prosthetic heart valve, wherein the end regions of the plurality of engagement struts are position proximally beyond the first set of radial struts and distally of the second set of radial struts.

In some aspects, the techniques described herein relate to a prosthetic heart valve, wherein the plurality of engagement struts form a first curve which curves around to about 180 degrees, a first straight portion with a length within an inclusive range of about 3 mm and about 10 mm, a second curve curving in an opposite direction of curve within an inclusive range of about 90 degrees to about 150 degrees, a rounded portion with a length within an inclusive range of about 2 mm to about 10 mm.

In some aspects, the techniques described herein relate to a method of delivering a prosthetic heart valve, including: advancing a delivery device in proximity of a native valve, the delivery device including a prosthetic valve having a framework; exposing distal end of the framework including a distal end of a cylindrical body portion and a plurality of leaflet engagement struts connected near the distal end of the cylindrical body portion; allowing the leaflet engagement struts to bend towards a proximal end of the cylindrical body portion and position native leaflets of the native valve between the leaflet engagement struts and the cylindrical body portion; and, completely releasing a remaining portion of the framework within the delivery device.

In some aspects, the techniques described herein relate to a prosthetic heart valve, including: a body portion having a generally cylindrical shape; an atrial flange portion extending radially and annularly outward from an inflow end of the body portion; and, a leaflet engaging portion; wherein the atrial flange portion and the leaflet engaging portion are configured to axially overlap each other at radially adjacent position within an inclusive range of about 0.1 mm and about 10 mm.

In some aspects, the techniques described herein relate to a prosthetic heart valve, including: a body portion having a generally cylindrical shape; an intra-annulus sealing portion including a plurality of struts positioned radially outside of the body portion and configured to engage an interior of a native valve annulus; and, a leaflet engaging portion including a plurality of engagement struts connected at an outflow end of the body portion and extending in an inflow direction along an outside of the body portion.

In some aspects, the techniques described herein relate to a prosthetic heart valve, further including an atrial flange portion extending radially outward from an inflow end of the body portion; and wherein the intra-annulus sealing portion extends distally from the atrial flange portion.

BRIEF DESCRIPTION OF THE DRAWINGS

These and other aspects, features and advantages of which embodiments of the invention are capable of will be apparent and elucidated from the following description of embodiments of the present invention, reference being made to the accompanying drawings, in which

FIG. 3 is a top view of a framework of the prosthetic heart valve support structure of FIG. 1.

FIG. 4 is a side view of the framework of the prosthetic heart valve support structure of FIG. 1.

FIG. 5 is a side view of the framework of the prosthetic heart valve support structure of FIG. 1.

FIG. 39 is an enlarged view of a framework of the prosthetic heart valve of FIG. 23.

FIG. 40 is an enlarged view of a framework of the prosthetic heart valve of FIG. 23.

FIG. 41 is an enlarged view of a framework of the prosthetic heart valve of FIG. 23.

FIG. 42 is an enlarged view of a framework of the prosthetic heart valve of FIG. 23.

FIG. 43 is an enlarged view of a framework of the prosthetic heart valve of FIG. 23.

FIG. 44 is a cross-sectional view of a framework of the prosthetic heart valve of FIG. 23.

DETAILED DESCRIPTION

Figure 1:
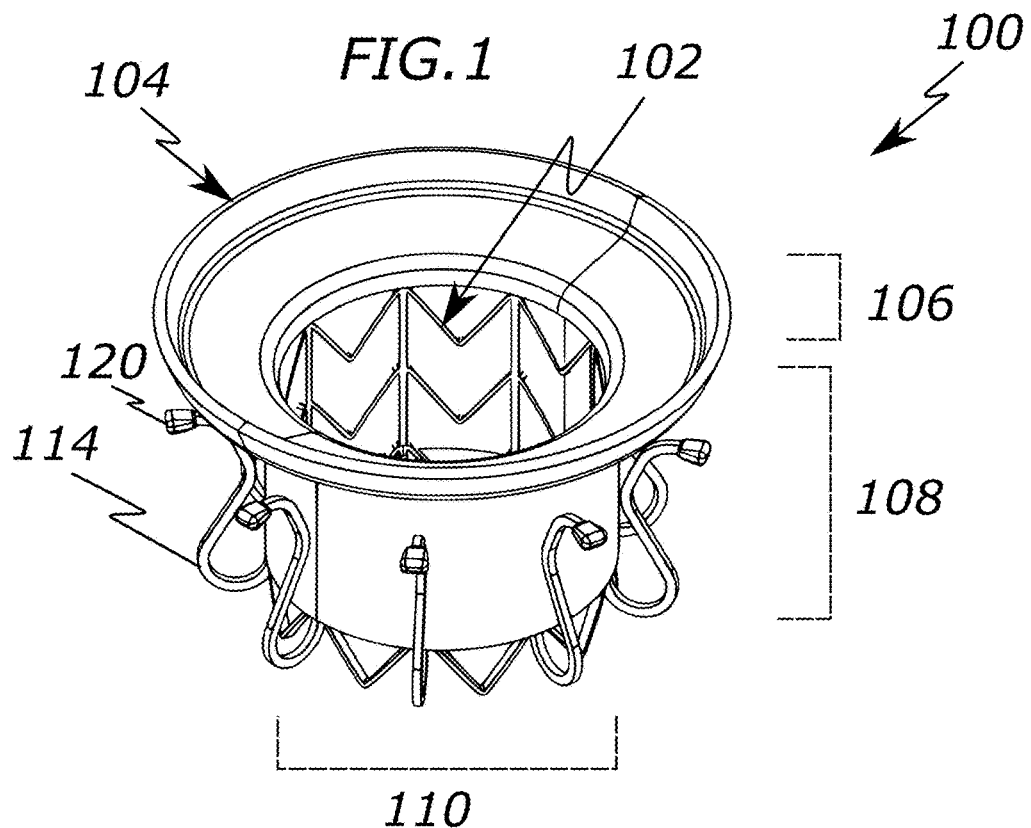
FIG. 1 is a perspective view of a prosthetic heart valve support structure.

Specific embodiments of the invention will now be described with reference to the accompanying drawings. This invention may, however, be embodied in many different forms and should not be construed as limited to the embodiments set forth herein; rather, these embodiments are provided so that this disclosure will be thorough and complete, and will fully convey the scope of the invention to those skilled in the art. The terminology used in the detailed description of the embodiments illustrated in the accompanying drawings is not intended to be limiting of the invention. In the drawings, like numbers refer to like elements.

While different embodiments may be described in this specification, it is specifically contemplated that any of the features from different embodiments can be combined together in any combination. In other words, the features of different embodiments can be mixed and matched with each other. Hence, while every permutation of features from different embodiments may not be explicitly shown, it is the intention of this specification to cover any such combinations.

The present specification is generally directed to prosthetic or artificial heart valves. These heart valves may be used to replace any of the native heart valves (e.g., aortic valve, mitral valve, pulmonary valve, or tricuspid valve), however, the artificial heart valves of this specification may be particularly useful for replacing a mitral or tricuspid valve.

Generally, the present artificial heart valves include a support structure that supports artificial valve leaflets or similar mechanisms that allow blood to generally flow in only one direction through the artificial heart valve. This specification focuses mostly on aspects of the support structure and therefore the figures may not all disclose artificial leaflets or similar structures therein. However, it should be understood that the use of leaflets and similar structures with the support structures are specifically contemplated. In other words, while much of this disclosure may focus on aspects of artificial valve support structures, the artificial valve as a whole is specifically included as part of the present invention.

When referring to the artificial valves and support structures in this specification, the terms "top end," "inflow end," and similar variants may be used interchangeably to mean an end of the device through which blood normally first enters the valve/device. For example, referring to a tricuspid valve, the end of the device in or closes to the right atrium. The terms "bottom end," "outflow end," and similar variants may be used interchangeably to mean an end of the device through which blood normally exits the valve/device. For example, referring to a tricuspid valve, the end of the device in or closes to the right ventricle. In addition, the artificial valves and support structures in this specification may be referred to as having proximal ends/portions and distal ends/portions in the context of a delivery device/catheter.

Typically, the term proximal indicates a portion or direction along the delivery device closer to the physician and distal indicates a portion or direction along or away from the delivery device in the opposite direction of the physician. In some of the examples described in this specification, the top or inflow end of the support structure may also be the proximal end, and the bottom or outflow end of the support structure may also be the distal end.

Generally, some of the artificial valve support structures of this specification include a body portion, an atrial flange portion, and a leaflet engaging portion. These features may take on different shapes, depending on whether the support structures are in a radially compressed configuration for deployment or a radially expanded configuration after deployment.

When the support structure is in its expanded configuration, the body portion may have a generally cylindrical shape with a passage extending between an inflow end and an outflow end. Alternatively, the body portion may have a generally concave, convex, or funnel shape, or may have a middle region with an increased or decreased diameter relative to the ends (e.g., hourglass shape or "bulging middle"). Typically, artificial leaflets or similar valve structures are fixed, mounted, or connected within the passage, such as at the middle or at either end of the passage. These artificial leaflets or similar valve structures can be tied to the body portion, connected with adhesive, or connected by similar means.

In the expanded configuration of the support structure, the atrial flange portion is a flange, lip, projection, or overhang that forms a generally annular region that extends radially outward from an inflow end of the body portion. The atrial flange portion may help seal around an inflow end of the device with the annulus of the native valve being replaced, thereby preventing blood from circumventing the passage of the body portion. In that respect, it may be desirable for the atrial flange portion to conform to the shape of the annulus of the valve. The atrial flange may extend completely and continuously around the entire circumference of the body portion or may only extend partially around the circumference of the body portion (e.g., two or more segments or a plurality of struts).

In the expanded configuration of the support structure, the atrial flange portion may be relatively flat or may have one or more curved surfaces. Additionally or alternatively, the flange may be generally perpendicular to an axis of the body portion or may radially extend at any angle 0 and 180 degrees relative to said axis. In one example, the atrial flange has an initial angle of about 110 degrees (plus or minus 10 degrees) bending slightly towards the direction of the annulus and then further bends upward (e.g., away from the annulus) to conform to the walls of the atrium. In some instances, it may be helpful for the atrial flange to generally conform to a top or inflow surface of a valve annulus (e.g., mitral or tricuspid valve annulus), as well as sidewalls of the surrounding atrium. Hence, depending on the length of the atrial flange, it may be helpful for the end region of the atrial flange to bend or be angled such that its edges are direction generally in an inflow direction similar to the walls of the right/left atrium (e.g., a similar angle to the longitudinal axis of the body portion).

In the expanded configuration of the support structure, the leaflet engaging portion may be positioned radially around the outside of the body portion in a manner to capture the native valve leaflets of the patient between the leaflet engaging portion and the body portion of the support structure. In one example, the leaflet engaging portion may be a plurality of struts and/or may be a continuous radial member. The leaflet engaging portion may further be connected to the body portion at or near an outflow end of the body portion and extend towards the inflow end of the body when the support structure is in its fully expanded configuration. The leaflet engaging portion may include one or more curved regions, such as a curved region near the free end(s) of the leaflet engaging portion that curves radially outward so as to engage an outflow surface of a native annulus of a native heart valve. Additionally or alternatively, the leaflet engaging portion may include one or more curves that position at least a portion of the leaflet engaging structure closer to or in contact with the body portion to help pinch or engage the native valve leaflets. Alternatively, the leaflet engaging portion may be spaced with a gap (e.g., uniform or non-uniform) with the body portion.

In the compressed configuration of the support structure, the body portion may be radially or diametrically compressed. The atrial flange may also be radially compressed and may further be 1) folded proximally or in an inflow direction such that its free end(s) are positioned further away from the body portion, or 2) may be folded distally or in an outflow direction such that the atrial flange is pressed against the body portion. The leaflet engaging portion may be 1) folded distally or in an outflow direction such that its free end(s) are positioned further away from the body portion, or 2) may be folded proximally or in an inflow direction such that the leaflet engaging portion is pressed against the body portion.

In some examples, it can be helpful to have the leaflet engaging portion folded distally in a delivery device in its compressed configuration such that its free end(s) are positioned away from the body portion. As the support structure (and the valve as a whole) is pushed out of or otherwise unrestrained from a delivery device, the free end(s) of the leaflet engaging portion will exit and be exposed first. As the free end(s) are further exposed, they will begin to bend radially outward or away from the body portion. If positioned beyond the native leaflets of the valve, the leaflet engaging portion will continue bending as more is exposed until its free end(s) are angled in an inflow direction, thereby positioning themselves between the radial outside of the native valve leaflets and the outflow track beyond the native valve annulus. As the support structure fully expands, the native valve leaflets remain trapped or engaged between the leaflet engaging portion and the body portion. This functionality should be understood to also be a method of deployment of the support structure.

In some examples, it can be helpful to construct the support structure such that in its expanded configuration, the end(s) of the leaflet engaging portion and the atrial flange portion each contact and therefore pinch or engage each side of the native valve annulus (or nearby tissue). This may help provide a better seal to the atrial flange portion to prevent blood from bypassing the artificial valve or creating a paravalvular leak. This may also help maintain the artificial valve in its intended position within a patient's heart.

In some examples, it can be helpful to construct the support structure such that in its expanded configuration, the end(s) of the leaflet engaging portion are positioned at a more proximal location or further in an inflow direction than at least some radially-adjacent portions (e.g., struts) of the atrial flange portion. When these portions are viewed from a side perspective, they overlap each other with regard to the axial position of their ends. This may be particularly helpful in two respects. First, this arrangement forces the leaflets and the annulus to be positioned over the leaflet engaging portion and then below the lower portion flange (e.g., lower radial strut), forcing the leaflets/annulus into an alternating or wave-like shape. Hence, the leaflet engaging portion and the atrial flange portion tend to pinch the leaflets/annulus and create a paperclip effect. Second, this arrangement may hold the material covering on the underside of the atrial flange portion taut around the top of the leaflet engaging portion so that there is good contact between the material covering and the leaflets/annulus to promote sealing, healing, and possibly tissue in-growth.

The support structure may have different approaches to its construction. In one example, the support structure comprises an underlying framework and a material covering placed onto or over part or all of the framework.

The framework may be composed of a shape memory material which has a specific shape imparted to it and which it returns to after being constrained. Example shape memory materials include Nitinol and similar alloys.

The framework may be composed of an entire single unitary framework. For example, the framework may be created from a shape memory tube (e.g., Nitinol) that is laser cut and then heat set to its desired expanded shape. Alternatively, a plurality of shape memory struts/shapes may be welded or otherwise connected together and then the desired expanded shape imparted to the connected struts/shapes.

The framework may also be composed of separate components that are connected to each other, either by welding, tying, adhesive, or via each component being separately connected to the material covering (i.e., the material covering interconnects the components). For example, the body portion, the atrial flange portion, and the leaflet engaging portion may all be separate components (e.g., welded together or connected via the material covering).

Some components of the framework may be composed of different types and structures material. For example, the body portion may be composed of a plurality of braided shape memory wires while the atrial flange portion and the leaflet engaging portion may be composed of non-braided shape memory struts/shapes (e.g., laser cut Nitinol components). In another example, the body portion and the leaflet engaging portion may be composed of non-braided shape memory struts/shapes (e.g., laser cut Nitinol components) and the atrial flange portion may be composed of a flexible polymer or similar material (e.g., silicone, PET, EPTFE etc.).

The framework may have different thicknesses in different areas (i.e., not only different lengths and widths, but thickness of the framework material itself). For example, the atrial flange portion may have a larger thickness than the body portion. In another example, the leaflet engaging portion may have a larger thickness than the body portion.

Certain components of the framework may be composed of elongated arms or struts without the material covering located on them. For example, the leaflet engaging portion may be composed of a plurality of struts positioned and connected at circumferential locations around the body portion. These locations can be either uniformly spaced or non-uniformly spaced only in certain areas. However, these arms or struts may have a coating and/or caps on their distal end. For example, the arms or struts may have a flexible coating that helps frictionally engage the leaflets and an end cap on the free ends of the arms/struts that is also composed of a flexible material to help minimize tissue damage during deployment and chronic implantation. Such a coating/cap may be composed of pericardial tissue, EPTFE, textile material, PET, polyurethane, silicone, and similar materials. The elongated arms or struts may all have the same length or may have different lengths, such as alternating between longer and shorter lengths.

The material covering may be connected to or otherwise positioned on part or all of the framework. Additionally or alternatively, the material covering may be disposed on only the inside of the framework, only the outside of the framework, or on both the inside and outside of the framework. In one example, the material covering is positioned on the body portion and the atrial flange portion, but not on the leaflet engaging portion. In another example, the material covering is positioned only on the atrial flange portion. In another example, the material covering is positioned only on the body portion. Additionally or alternatively, the material may create openings or other shapes (e.g., triangular edges) against the framework.

The material covering may be composed of a biocompatible, flexible material. The material covering may be a solid, non-porous sheet (e.g., a polymer sheet) or a woven fabric. Example materials include textile material, EPTFE sheets, PET sheets, Silicone, polyurethane, similar materials, or derivatives thereof. This material covering may also be configured, at least in certain areas, to encourage ingrowth of tissue.

The valve leaflets may be connected to the body portion, such as near the middle or near either end of the body portion. Generally, the valve leaflets are configured to open to allow blood flow from the inflow end (e.g., from the left/right atrium) and remain closed against blood pressure from the outflow end (e.g., from the left/right ventricle). The valve component may include one, two or three leaflets. The valve leaflets may be individually attached to the support structure or may all be attached to each other into a valve assembly that is then attached to the support structure. The valve leaflets may be attached to the body portion in a normally open or a normally closed position. The shape of the valve leaflets is such that the leaflets take a natural cusp like shape similar to a native aortic valve. or similar valve. This shape along with the covering material of the body structure can create a sinus like shape similar to a valve sinus to allow for favorable flow conditions and beneficial blood flow washout to prevent stasis locations and thrombus formation. The valve leaflets may be attached to the valve body in a configuration to allow for an amount of overlap or coaptation at the free edge with a range of 0 to 20 mm. There may be an intentional gap in the valve leaflet coaptation to allow for a small amount of blood to leak through the valve so as to not over pressure the heart after the new valve is in place. The valve leaflets may be composed of an artificial material or from natural biological material. The valve leaflets may be processed using anti-calcification and tissue fixation processes to prevent the human body from rejecting the implanted device and to also prevent leaflet calcification. The tissue may be processed in a condition that allows for the valve prosthesis to be stored and sterilized in glutaraldehyde or in dry storage after other means of sterilization such as ETO. The tissue can also be processed with or coated with antithrombotic chemicals or coatings.

The support structure may also include features that allow engagement with a delivery device to assist in deployment of the support structure. Additionally or alternatively, features may be included that allow the support structure to be recaptured after at least partial deployment from the delivery device. For example, the support structure may include one or more apertures or enlargements, such as on its framework, that are releasably engaged with portions of the delivery device. The apertures or enlargements may be included at or near the proximal or inflow end of the support structure when in its compressed configuration. For example, the apertures or enlargements may be located at locations at the edge of the atrial flange portion and/or at locations near the end of the body portion. The delivery device may include a breakable thread that passes through/around the apertures/enlargements, depressions in an inner pusher that capture the apertures/enlargements, hooks, posts, loops, stent-like mesh, or similar mechanisms such that a physician may advance, retract, and/or release the support structure from the delivery device.

Any of the support structures in this specification may be delivered from one of several known heart valve delivery devices. For example, the devices in U.S. Pub. No. 2017/0165064, 2019/0008640, and 2022/0287836, the content of which is hereby incorporated by reference.

FIGS. 1-13 illustrate various aspects of one example of a support structure 100 of an artificial valve in its expanded configuration. As seen best in FIGS. 1 and 2, the support structure 100 generally includes a body portion 110, an atrial flange portion 106, and a leaflet engaging portion 108.

In the present example, the body portion 110 has a generally cylindrical shape, though other shapes are possible, such as an hourglass shape, a conical shape, a concave shape, or a convex shape.

In the present example, the atrial flange portion 106 extends radially outward from a top end or an inflow end of the body portion 110. The atrial flange portion 106 may form a complete circular or annular shape beyond that of the body portion 110, though it may alternatively have other shapes such as an oval shape and may only extend around a portion of the circumference of the body portion 110 (e.g., flange regions on only opposite sides of each other).

Figure 2:
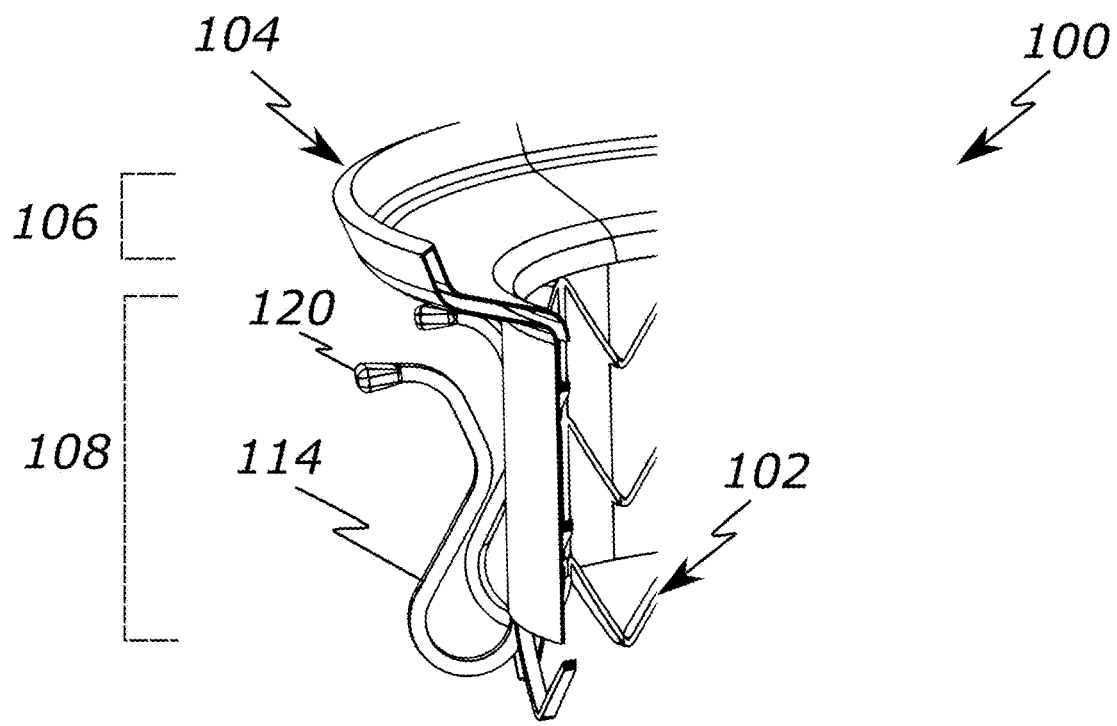
FIG. 2 is a cross-sectional view of the prosthetic heart valve support structure of FIG. 1.
Figure 6:
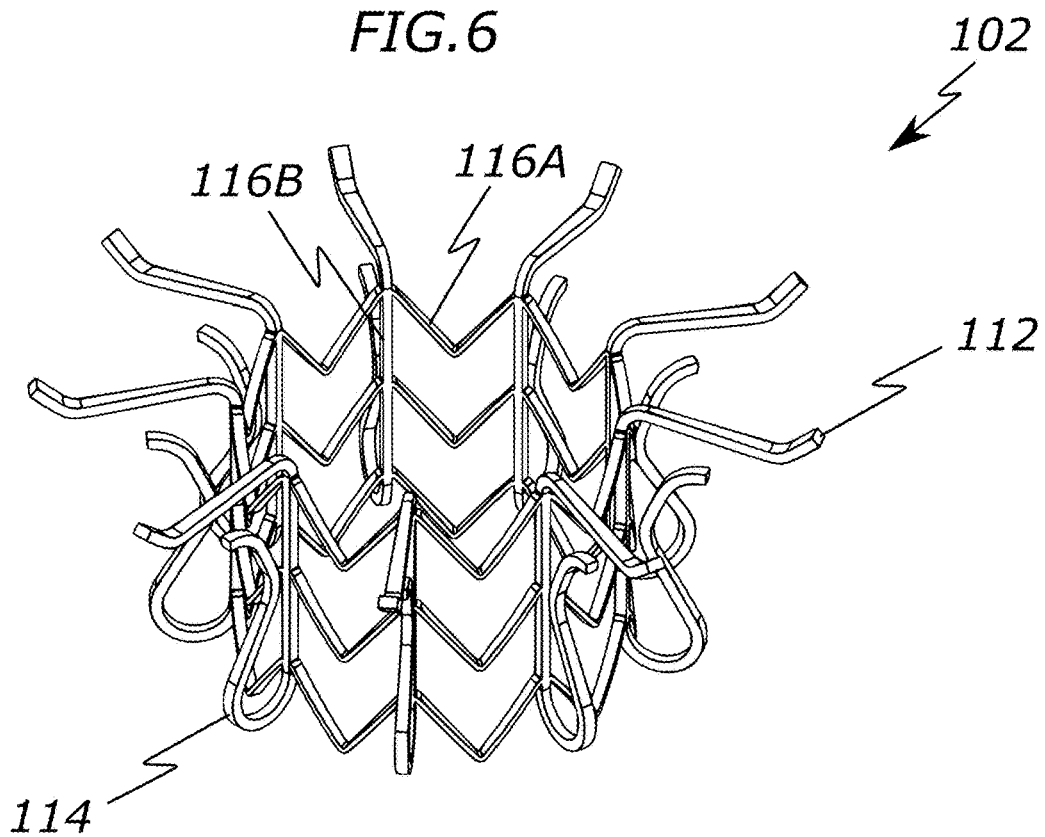
FIG. 6 is a perspective view of the framework of the prosthetic heart valve support structure of FIG. 1.
Figure 7:
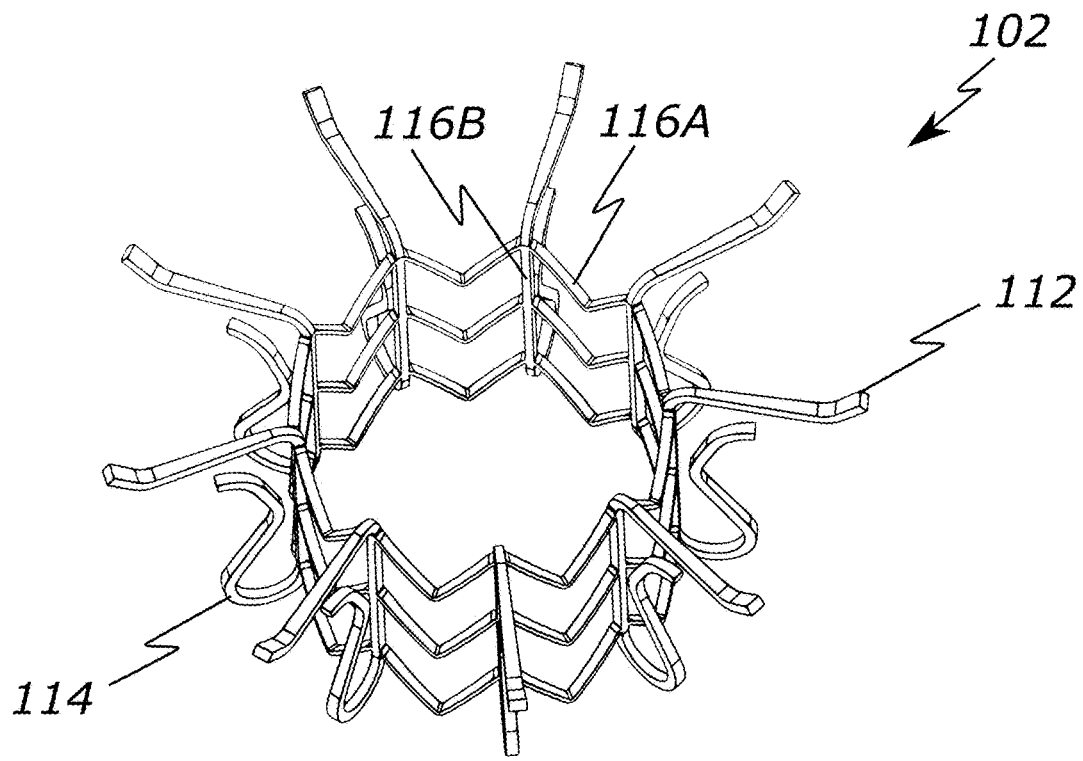
FIG. 7 is a perspective view of the framework of the prosthetic heart valve support structure of FIG. 1.
Figure 8:
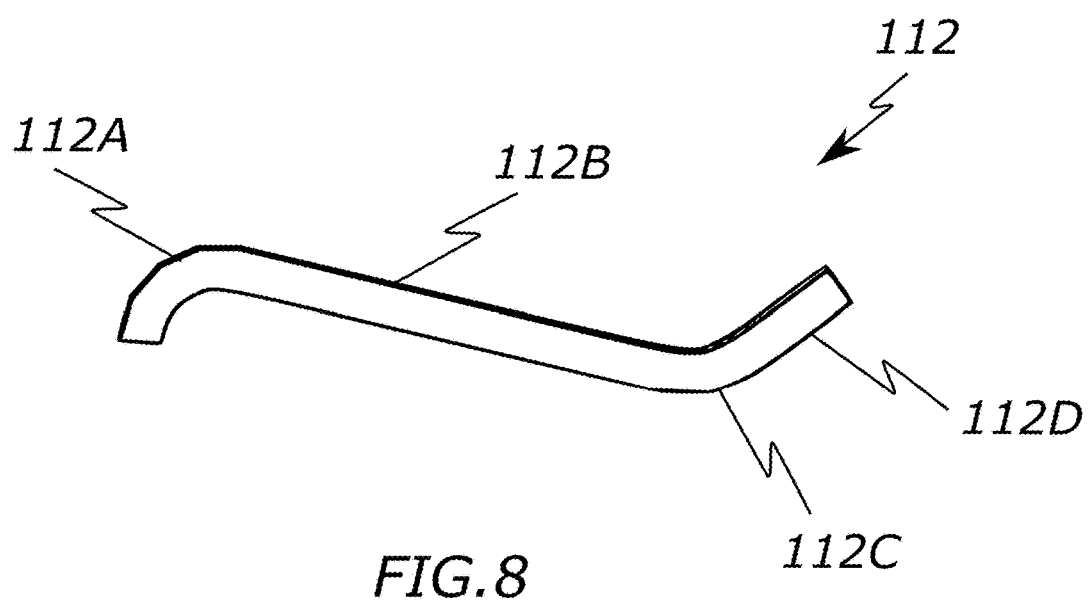
FIG. 8 is a strut of the framework of the prosthetic heart valve support structure of FIG. 1.

In the present example, the atrial flange 106 may have at least two regions having different angles relative to each other, as best seen in the cross-sectional view of FIG. 2. A first region initially extends radially away from the inflow end of the body portion 110. Relative to an axis extending through the inner passage of the support structure, the first region may have an angle within an inclusive range of about 70 degrees and 140 degrees (e.g., about 110 degrees). A second region radially extends from the first region and has an angle within an inclusive range of 120 degrees and 170 degrees (e.g., about 160 degrees). Generally, these two regions of the atrial flange portion 106 may help it conform to the top/inflow surface of the native valve annulus, as well walls or other areas of the atrium.

In the present example, the leaflet engagement portion 108 may comprise a plurality of engagement struts 114 that are connected at an outflow end of the body portion 110 and extend in an inflow or upward direction. As will be described in further detail later, the engagement struts 114 curve towards the body portion 110 and then away from the body portion 110, terminating with a cap member 120. The initial curve towards the body portion 110 may help pinch or engage the native leaflets with the body portion 110. The cap 120 may comprise a flexible or relatively softer material (e.g., pericardial tissue, EPTFE, PET, textile materials, silicone, polyurethane, or similar materials) to help prevent damage to the patient's heart tissue. The cap may be adhered to or otherwise connected to the very distal end of the engagement strut 114.

In the present example, the engagement struts 114 are positioned at equal distances from each other around the circumference of the body portion 110. Again, non-uniform positioning of these struts 114 is also possible, such as only on opposite sides of the body portion 110 or in locations that may help avoid chordae within the ventricle.

The support structure 100 in the present example includes a rigid framework 102 and a material covering 104 that is disposed over portions of the framework 102. The material covering 104 is positioned over all or most of an outside of the body portion 110 of the framework 102, over an outside of the atrial flange portion 106 of the framework 102, and around on an inner side of the atrial flange portion 106 of the framework 102. The engagement struts 114 are generally left uncovered by the material covering 104. As previously described, other variations are also possible, such as locating the material covering on only the inside, only the outside, and/or on any combination of the portions 106, 108, 110.

In the present example, the material covering 104 may be attached by adhesive, stitches, combinations thereof, and similar mechanisms. The material covering 104 may be composed of textile material, EPTFE sheets, PET sheets, and similar materials discussed elsewhere in this specification. In addition to the material covering 104, additional materials may be included on an underside of the atrial flange 106 to help create a better seal with the native valve annulus, such as hydrogel.

FIGS. 3-9 illustrate various aspects of the framework 102 in the present example. The body portion 110 of the framework 102 is composed of a plurality of elongated vertical body struts 116B and a plurality of horizontal body struts 116A. The vertical body struts 116B are generally parallel to an axis through the support structure's passage (i.e., an axis from the inflow end to the outflow end), while the horizontal body struts 116A are positioned around this axis in a circular shape.

The horizontal body struts 116A may form a "V" shape or a relatively sharp angle pointing towards the outflow direction, though the opposite direction is also possible. Each end of a horizontal body strut 116A connects to a vertical body strut 116B. The "V" shape of the horizontal body strut 116A provides a bend point at the apex of its "V" to increase and decrease its angle depending on whether the support structure 100 is in its compressed configuration or expanded configuration. In other words, the "V" shape facilitates this radial compression and expansion. Alternatively, other shapes with angles in them may also be possible for the horizontal body structure 116A, such as a "W" shape with two or more angles. In the present example, there are two rows of horizontal body struts 116A, though more rows are possible.

In one example, the body portion 110 of the framework 102 has a length within an inclusive range of about 14 mm to about 18 mm, and has a diameter within an inclusive range of about 27 mm to about 30 mm.

The atrial flange portion 106 of the framework 102 includes a plurality of flange struts 112. The shape of these flange struts 112 can be best seen in FIG. 8. Each flange strut 112 extends from one of the vertical body struts 116B and forms a first angle 112A within an inclusive range of about 90 degrees and 130 degrees, a relative straight portion 112B with a length within an inclusive range of about 3 mm and about 10 mm, a second angle 112C within an inclusive range of about 20 degrees and about 150 degrees, and a terminal portion 112D with a length within an inclusive range of about 1 mm and 7 mm (again, angles relative to an inflow/outflow oriented axis of the support structure 100). Generally, the specific angles and sizes may vary somewhat depending on the heart and valve size of the patient.

Figure 9:
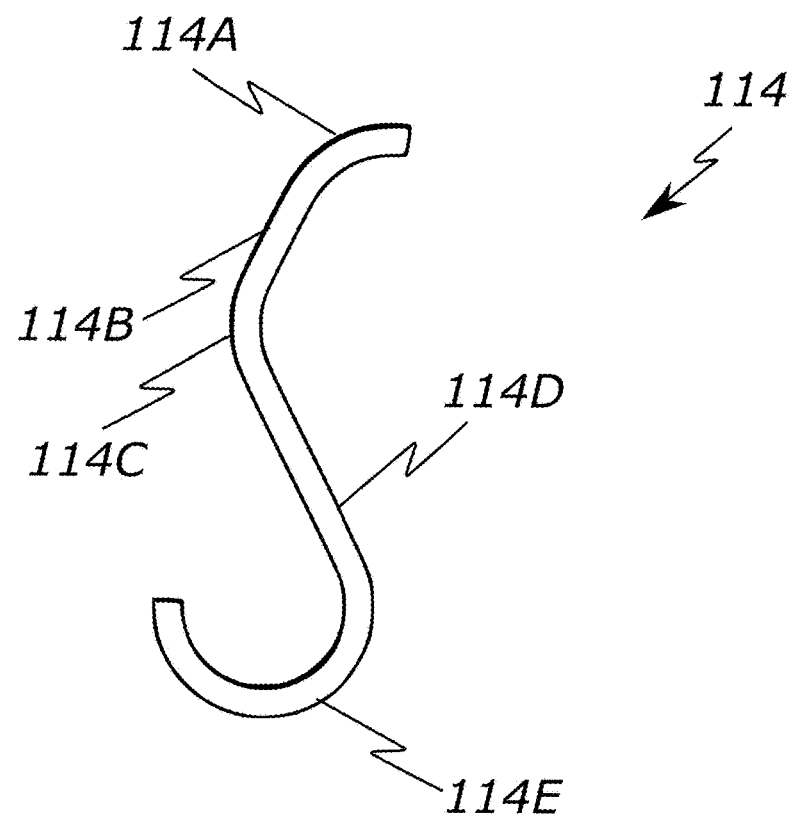
FIG. 9 is a strut of the framework of the prosthetic heart valve support structure of FIG. 1.

The leaflet engaging portion 108 of the framework 102 includes a plurality of engagement struts 114, the shape of which can be best seen best in FIG. 9. The leaflet engaging struts 114 are connected to the outflow end of the vertical body struts 116B. From the vertical body strut 116B, the engagement strut forms a first curve 114E which curves around beyond 180 degrees (e.g., an inclusive range of about 150 degrees to about 230 degrees), a first straight portion 114D with a length within an inclusive range of about 3 mm and about 10 mm, a second curve 114C curving in an opposite direction of curve 114D within an inclusive range of about 90 degrees to about 150 degrees, a second straight portion 114B with a length within an inclusive range of about 2 mm to about 10 mm, and finally a third curve 114A in the same direction as the second curve 114C and within an inclusive range of about 60 degrees and about 150 degrees. While these curves all generally occur in the same plane, it is possible to include additional curves that may take some of the engagement struts 114 out of a single plane (i.e., curving in multiple dimensions).

As previously discussed, the engagement struts 114 are not covered by the material covering 104 in the present example, but may be. Additionally, the engagement struts 114 may be coated or wrapped in a relatively softer material (e.g., a textile or EPTFE layer). Further, the ends of the engagement struts may include cap members 120 composed of similar materials or other materials described in this specification.

The framework 102 of the present example may be composed of a single unitary body, such as laser cut from a shape memory tube (e.g., Nitinol tube). Alternatively, one or more of the struts of the framework may be welded or otherwise attached to each other. Alternatively, some of the components may be separate from each other, only connected by other materials, such as the material covering 104 or other attachment mechanisms. For example, the body portion 110, the leaflet engagement portion 108, and/or the atrial flange portion 106 may not be directly attached to each other in any combination. If shape memory material is used for the framework 102, the framework may be cut to a desired pattern and then heat set to impart a desired shape in its expanded configuration.

Figure 10:
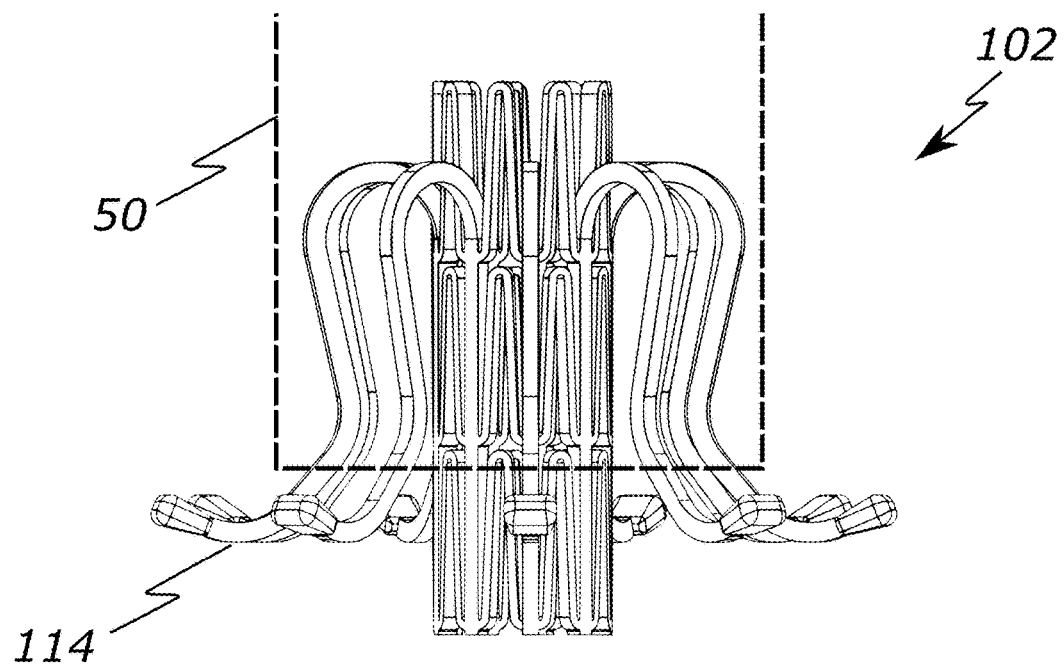
FIG. 10 is a compressed view of the framework of the prosthetic heart valve support structure of FIG. 1.
Figure 11:
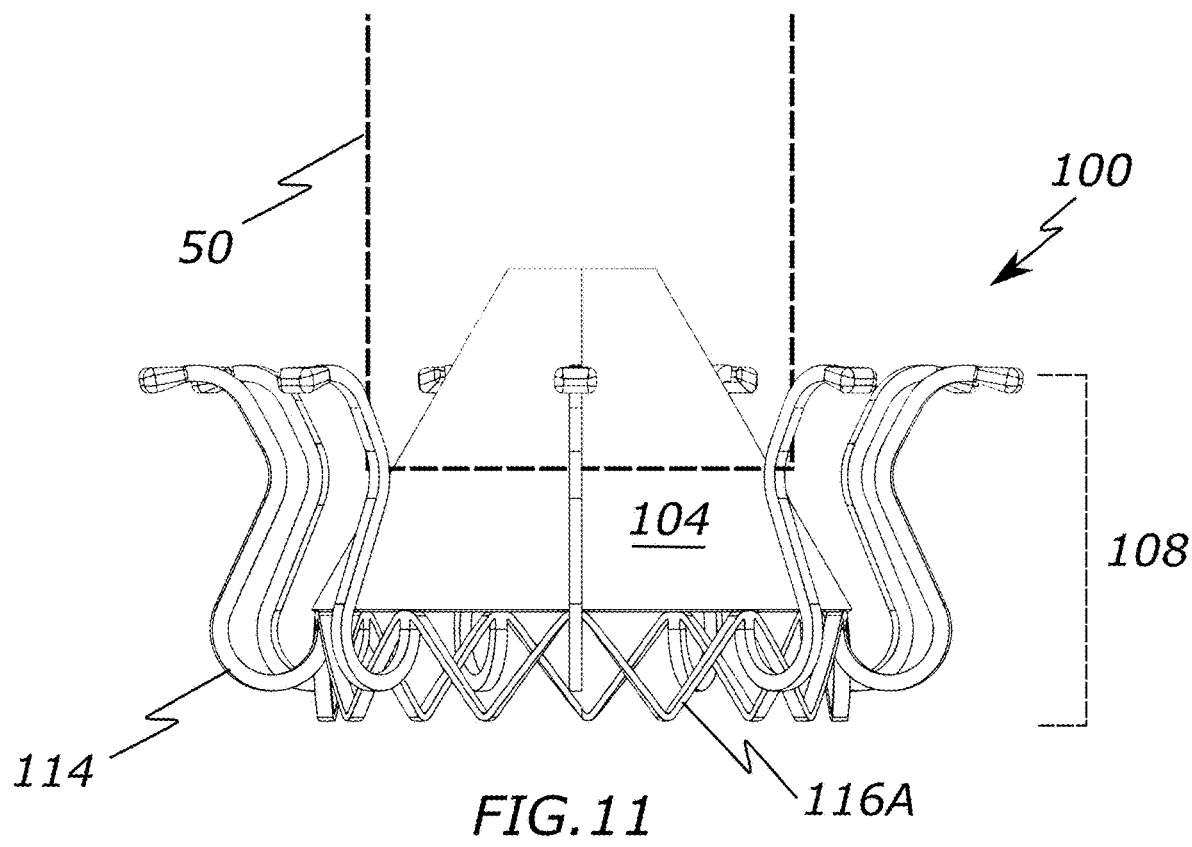
FIG. 11 is a partially compressed view of the framework of the prosthetic heart valve support structure of FIG. 1.
Figure 12:
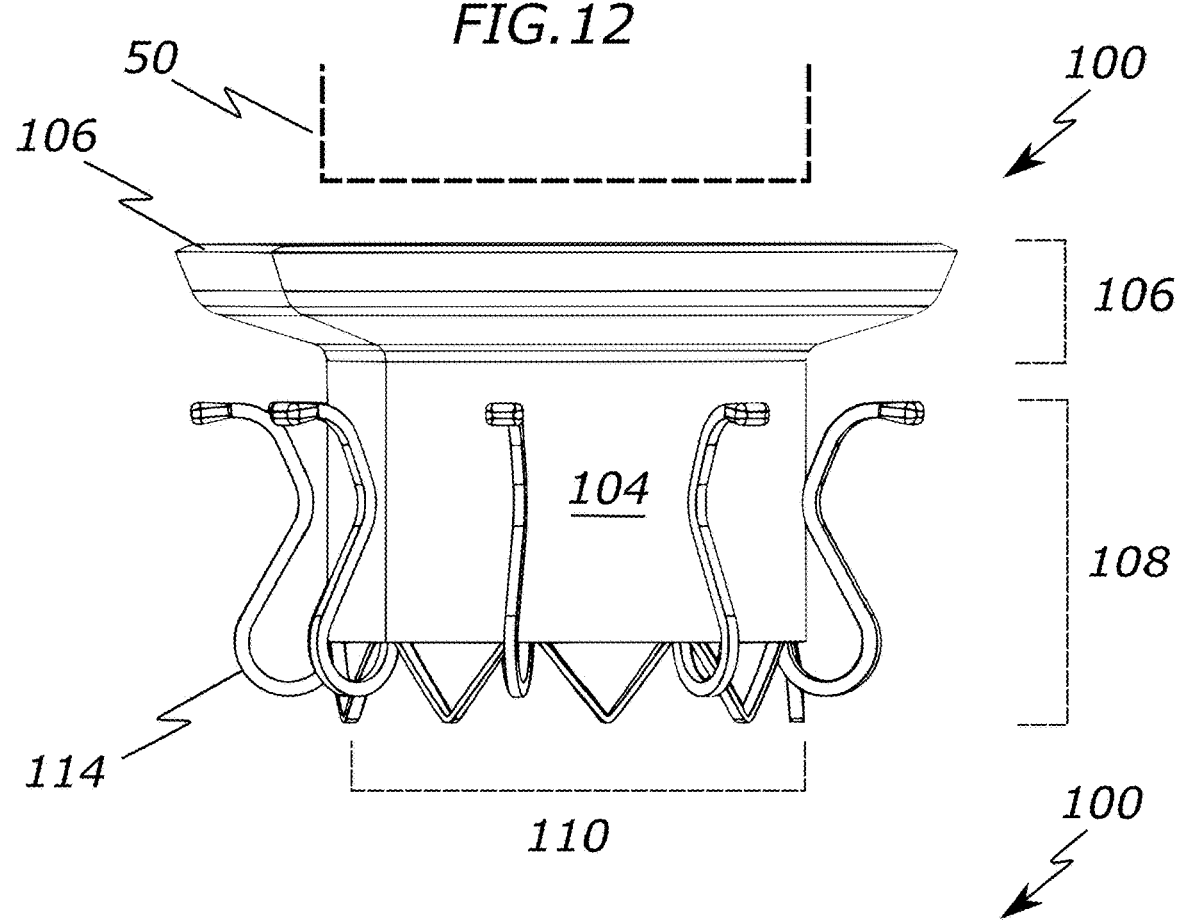
FIG. 12 is a view of the framework of the prosthetic heart valve support structure of FIG. 1 after deployment.

FIGS. 10-12 illustrate how the support structure 100 may deploy from a delivery catheter 50. In FIG. 10, the support structure 100 is illustrated mostly within with delivery catheter 50 (note, for clarity only the framework 102 is illustrated in this figure). As the support structure 100 begins to be pushed out, the free ends of the engagement struts 114 begin to radially expand outward.

In FIG. 11, the support structure 100 has moved further distally out of the delivery catheter 50. The distal or outflow end of the body portion 110 has radially expanded and the engagement struts 114 of the leaflet engagement portion 108 have completely escaped the delivery catheter 50 and have inverted themselves such that their free ends are now located towards a proximal or inflow end of the body portion 110.

Figure 13:
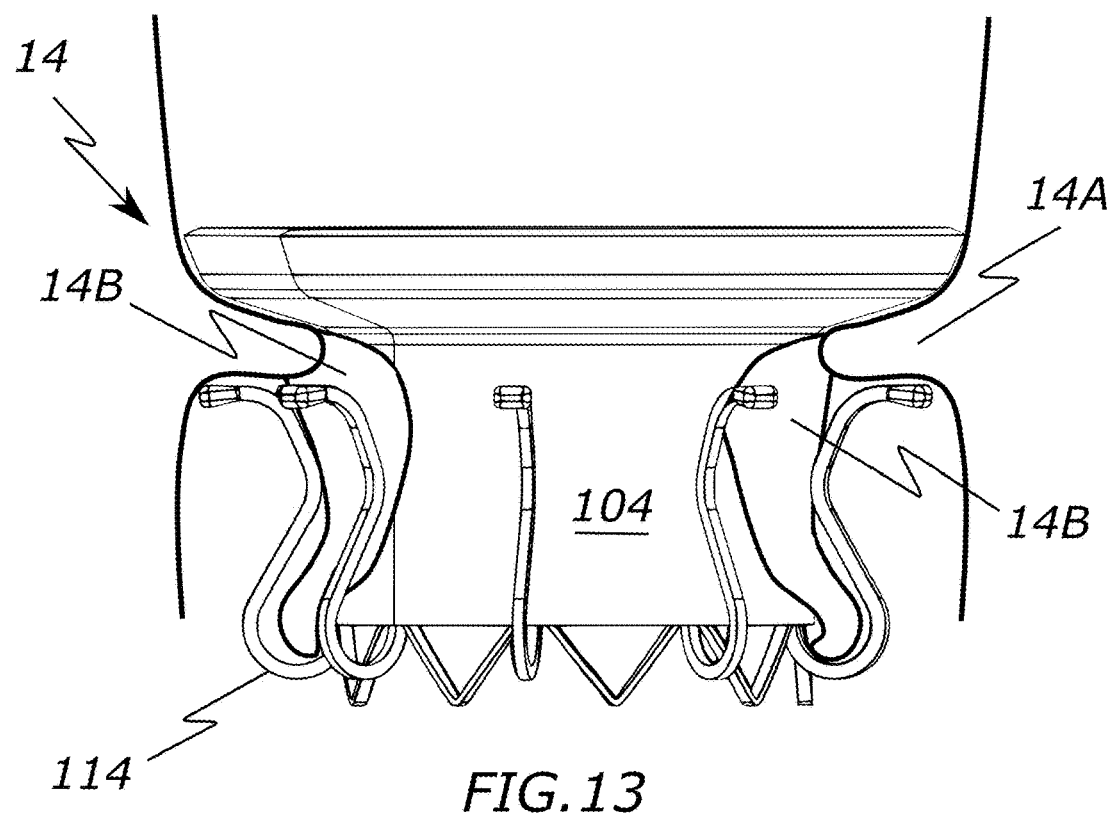
FIG. 13 is a view of the framework of the prosthetic heart valve support structure of FIG. 1 within a native valve.

In FIG. 12, the support structure is fully deployed to its expanded configuration. FIG. 13 illustrates the expanded configuration within a tricuspid valve 14. As can be seen, the engagement struts 114 have been positioned around the leaflets 14B so as to capture the leaflets 14B against the body portion 110. Additionally, it can be seen that the bottom of the atrial flange portion 106 contacts and engages a top portion of the valve annulus 14A, while the angled free ends of the engagement struts engage a bottom portion of the valve annulus 14A. Hence, the support structure 100 may better engage the annulus 14A and keep the valve leaflets 14B out of the way.

Figure 14:
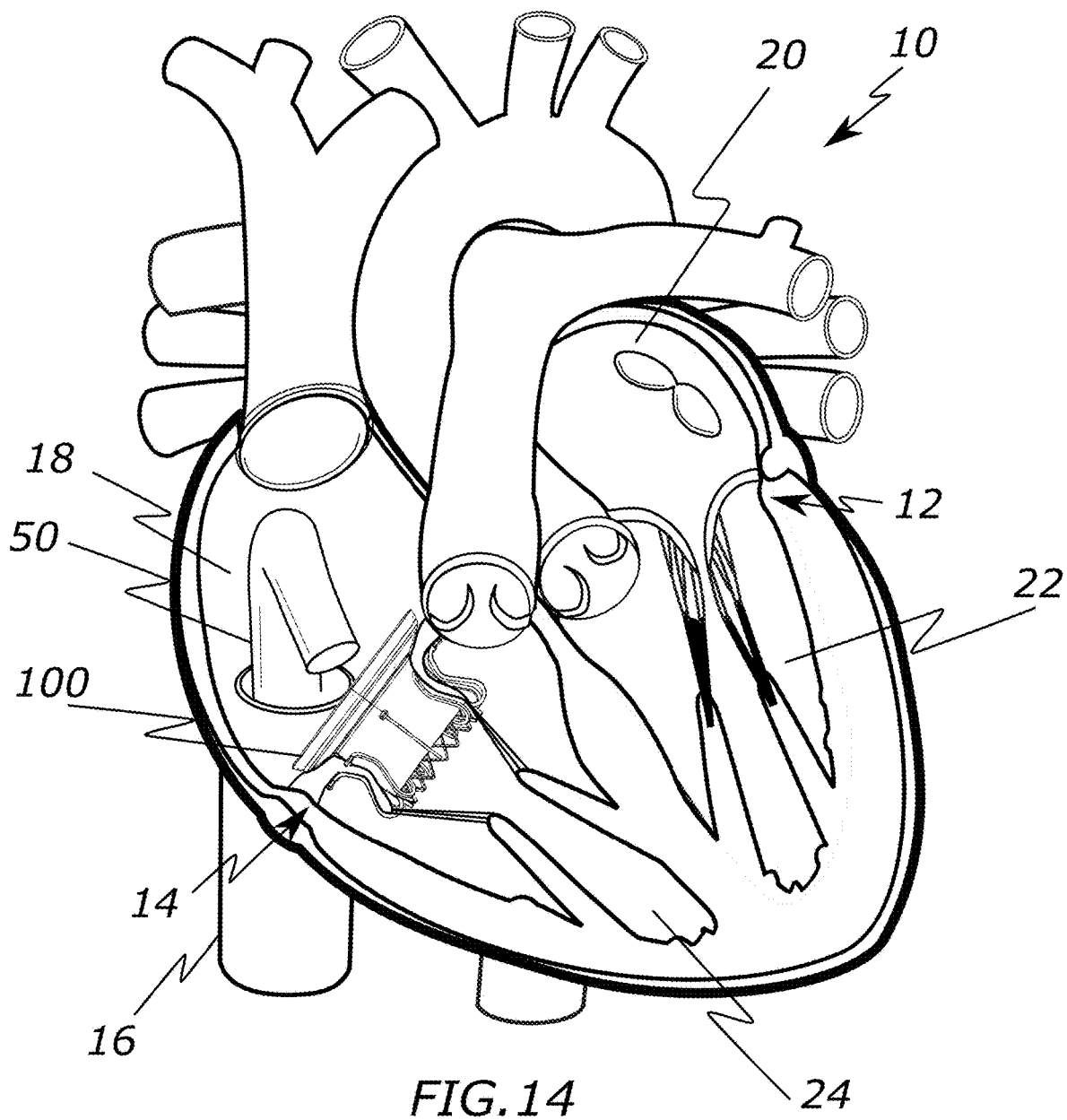
FIG. 14 is a view of the framework of the prosthetic heart valve support structure of FIG. 1 within a native valve.

FIG. 14 illustrates one approach to delivering a support structure 100 within a tricuspid valve 14 of a heart 10 by advancing a delivery catheter through the inferior vena cava 16 and into the right atrium 18, such that the support structure is delivered from an inflow or atrial end relative to the tricuspid valve 14.

Figure 15:
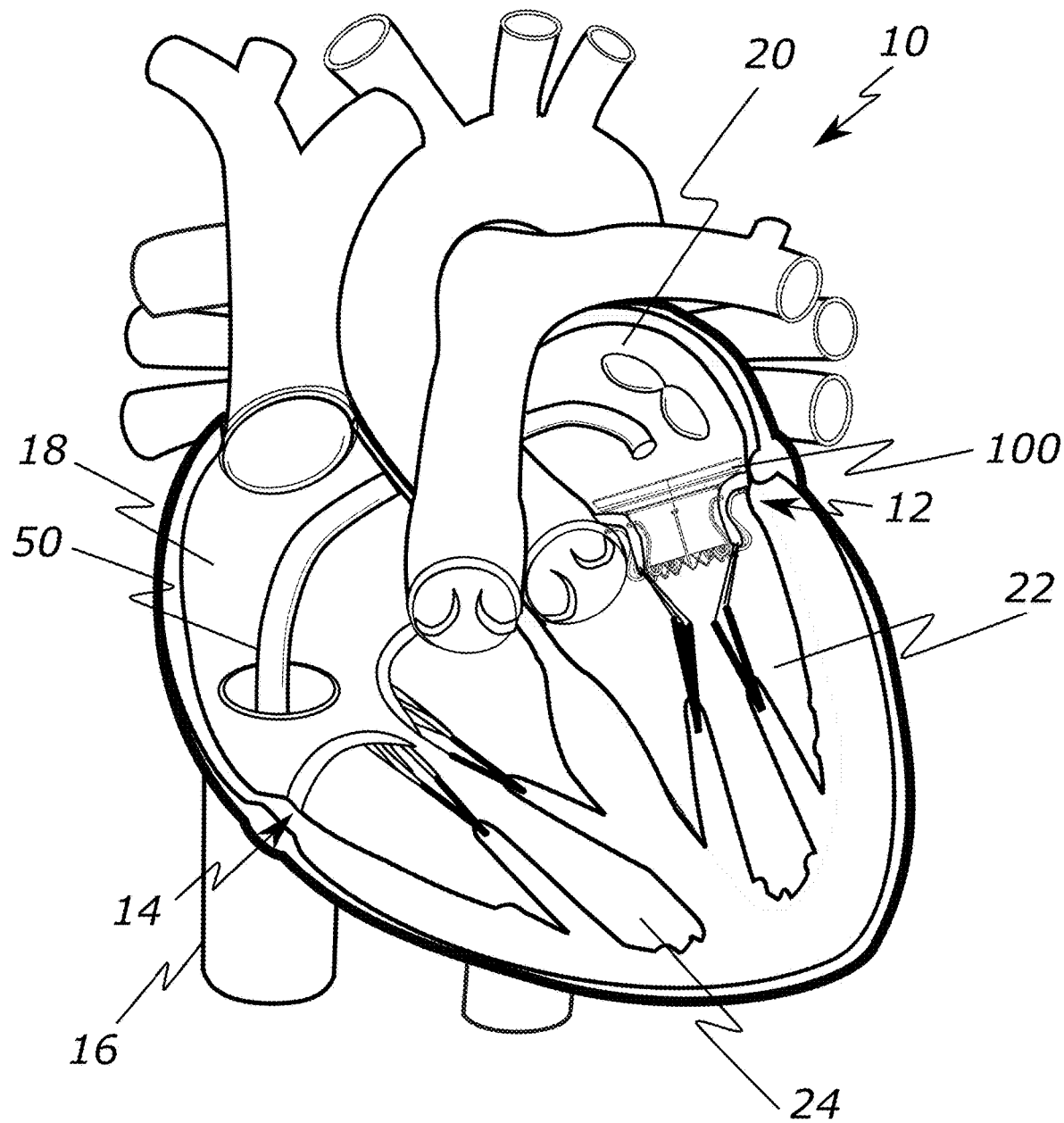
FIG. 15 is a view of framework of the prosthetic heart valve support structure of FIG. 1 within a native valve.
Figure 16:
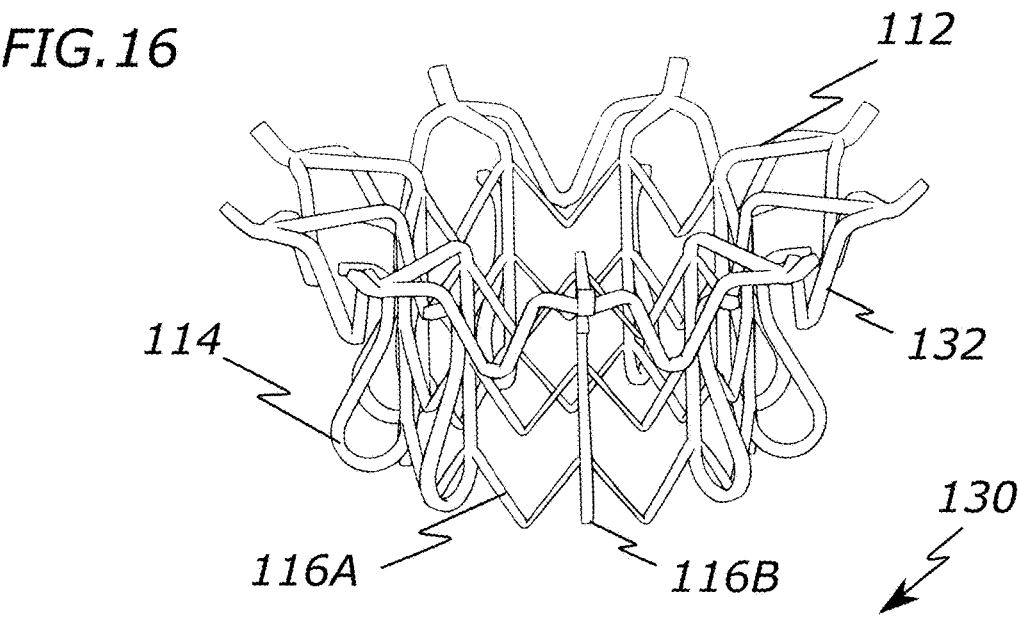
FIG. 16 is a perspective view of a prosthetic heart valve.
Figure 17:
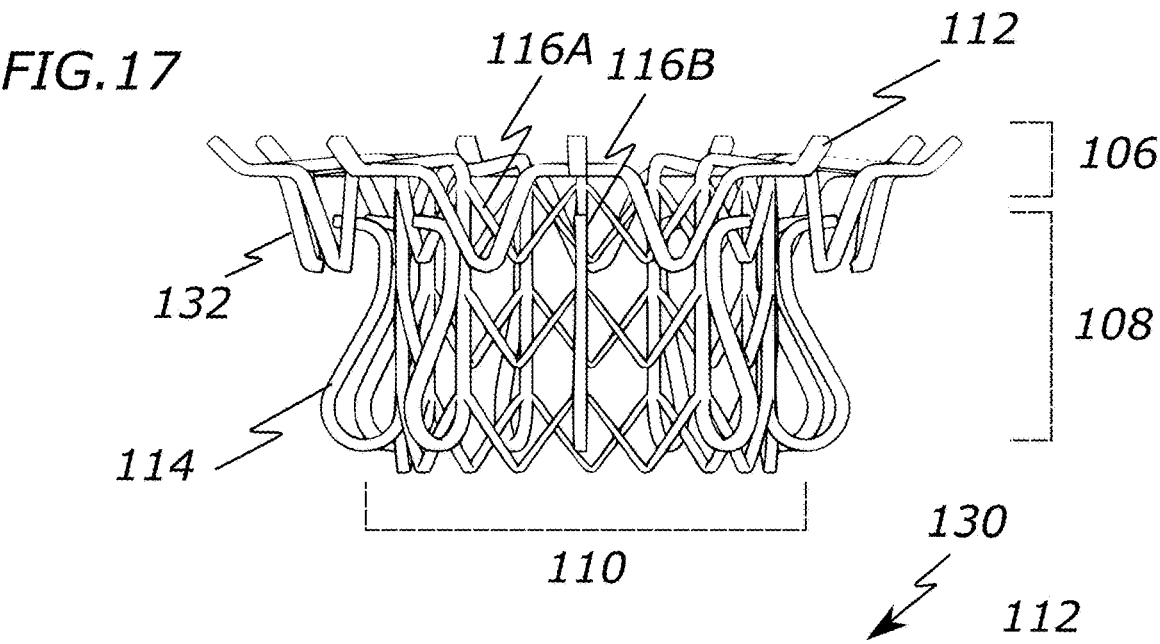
FIG. 17 is a side view of the prosthetic heart valve of FIG. 16.
Figure 18:
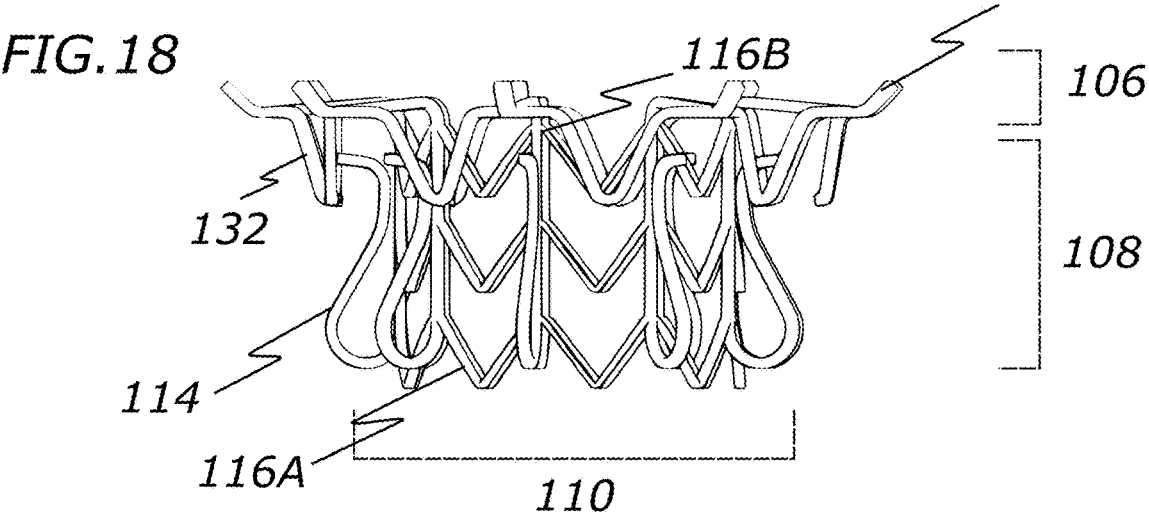
FIG. 18 is a side view of the prosthetic heart valve of FIG. 16.
Figure 19:
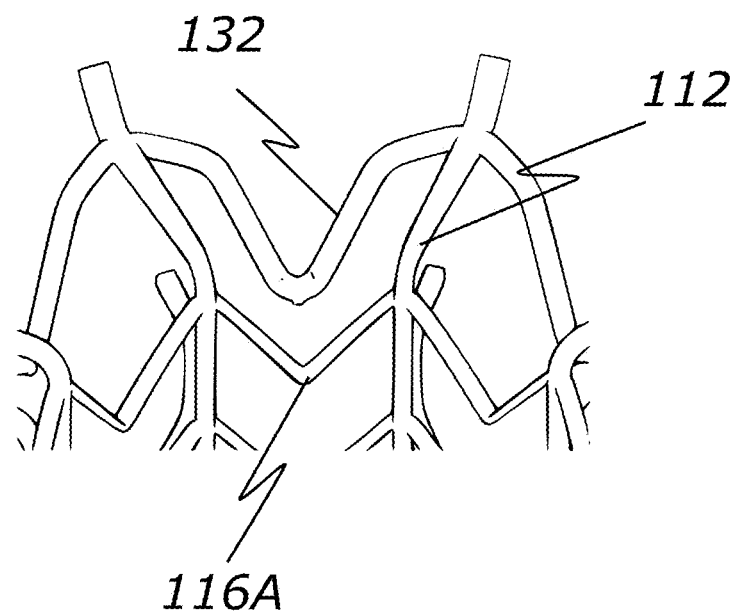
FIG. 19 is enlarged cross-sectional view of the prosthetic heart valve of FIG. 16.

FIG. 15 illustrates another approach to delivering a support structure 100 with a mitral valve 12 by performing a transeptal procedure to allow the delivery catheter to pass through the septum between the right atrium 18 and the left atrium 20. This allows the support structure to be delivered from an inflow or atrial end relative to the mitral valve 12.

Additional approaches to delivering the support structure 100 are also possible. For example, either valve 14, 20 may be approached from its respective ventricle (22, 24). In such cases, the support structure may be arranged in an opposite orientation as shown in FIGS. 10-12.

FIGS. 16-22 illustrate an embodiment of a framework 130 that is otherwise similar to the previously described framework 102. However, the framework 130 further includes a strut 132 that connects to two adjacent flange struts 112 and forms a "V" shape downward towards an outflow end of the framework 130. While this strut 132 may be considered part of the atrial flange portion 106, it may be positioned within the annulus of the valve while portions of the flange struts 112 remain on a top or atrial surface of the annulus of the native valve. Hence, the atrial flange portion 106 of this embodiment may be further considered to have a top sealing portion (i.e., flange struts 112) and an intra-annulus engaging/sealing portion (struts 132). In that manner, the framework 130 may better seal the framework/valve to prevent blood leakage around the framework/valve.

Figure 20:
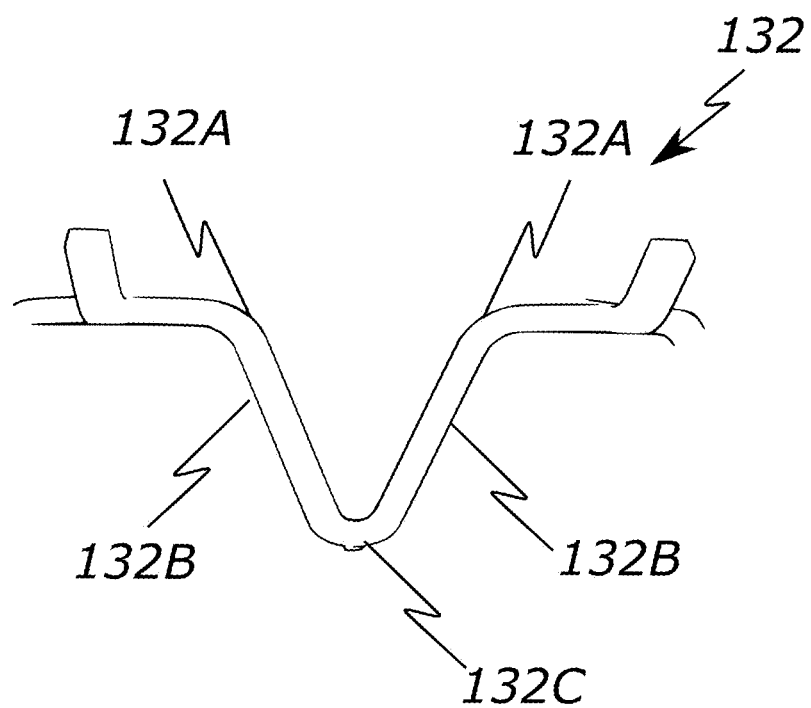
FIG. 20 is enlarged cross-sectional view of the prosthetic heart valve of FIG. 16.

As best seen in FIG. 20, the strut 132 initially extends relatively horizontal from the flange strut 112 and then forms a first angle 132A that may be within an inclusive range of about 135 degrees to about 180 degrees towards an outflow end of the framework 130. The strut 132 may further have a straight region 132B with a length in an inclusive range of about 3 mm to about 10 mm. Finally, the strut 132 forms a middle angle 132C, opposite of the first angle 132A within an inclusive range of about 90 degrees and about 120 degrees. The straight region 132B and angle 132A symmetrically repeat on the opposite side of the middle angle 132C, thereby creating a generally "V" shape between two of each of the flange struts 112.

Figure 21:
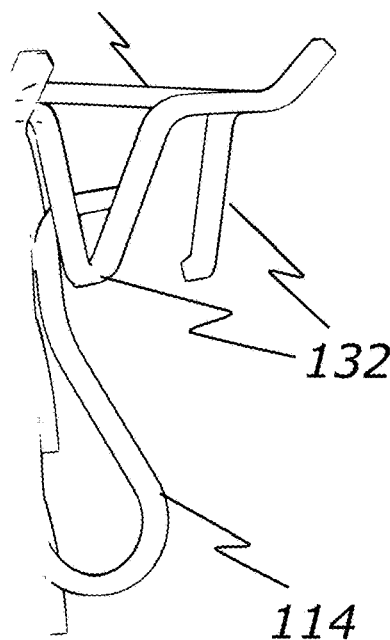
FIG. 21 is enlarged cross-sectional view of the prosthetic heart valve of FIG. 16.

As seen best in FIG. 21, the "V" shaped strut 132 may be further angled generally straight/parallel to an axis of the framework 130 or may be angled such that the tip of the "V" shape, or angle 132C, is positioned somewhat close to the body portion 110. In other words, the strut 132 may angle radially inwards toward the outflow end of the framework. This may help the "V" shape of the strut 132 to fit into and engage the annulus of the native valve. In one example, the strut 132 is angled radially inward within a range of about 0 degrees to about 30 degrees.

FIGS. 23-33 illustrate various aspects of another example of a support structure 150 that is generally similar to the previously described support structure 100, but includes several notable differences discussed further below. As seen best in FIG. 18, the support structure 150 generally includes a body portion 110, an atrial flange portion 106, and a leaflet engaging portion 108.

In the present example, the body portion 160 has a generally cylindrical shape, though other shapes are possible, such as an hourglass shape, a conical shape, a concave shape, or a convex shape.

In the present example, the atrial flange portion 156 extends radially outward from a top end or an inflow end of the body portion 160. The atrial flange portion 156 may form a complete circular or annular shape beyond that of the body portion 160, though it may alternatively have other shapes such as an oval shape and may only extend around a portion of the circumference of the body portion 160 (e.g., flange regions on only opposite sides of each other). As seen best in FIG. 23, the atrial flange portion 156 also generally forms a plurality of petal shapes, pointed shapes, or outwardly narrowing shapes, such that the width of each of these areas decreases as the distance from the body portion 160 increases.

Figure 22:
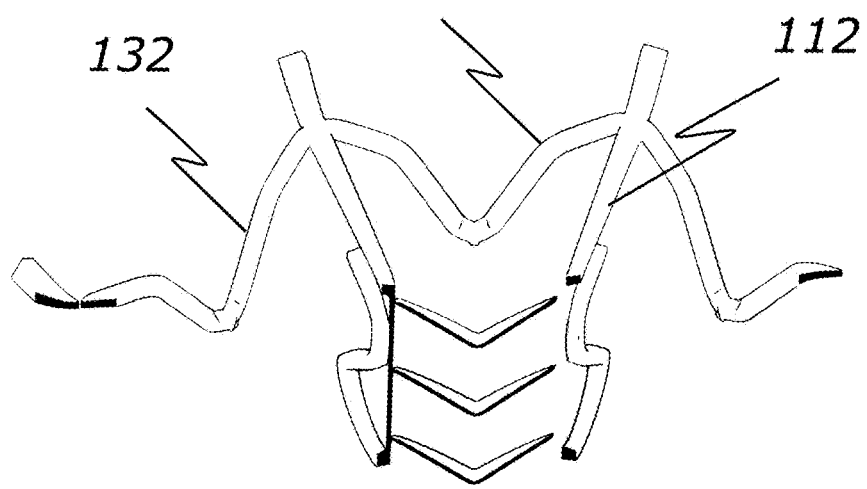
FIG. 22 is enlarged cross-sectional view of the prosthetic heart valve of FIG. 16.

In the present example, the atrial flange 156 may have at least two regions having different angles relative to each other, as best seen in the cross-sectional view of FIG. 22. A first region initially extends radially away from the inflow end of the body portion 160. Relative to an axis extending through the inner passage of the support structure, the first region may have an angle within an inclusive range of about 70 degrees and 140 degrees (e.g., about 120 degrees). A second region radially extends from the first region and has an angle within an inclusive range of 150 degrees and 220 degrees (e.g., about 200 degrees). Generally, these two regions of the atrial flange portion 156 may help it conform to the top/inflow surface of the native valve annulus, as well walls or other areas of the atrium or leaflet/annulus.

Figure 23:
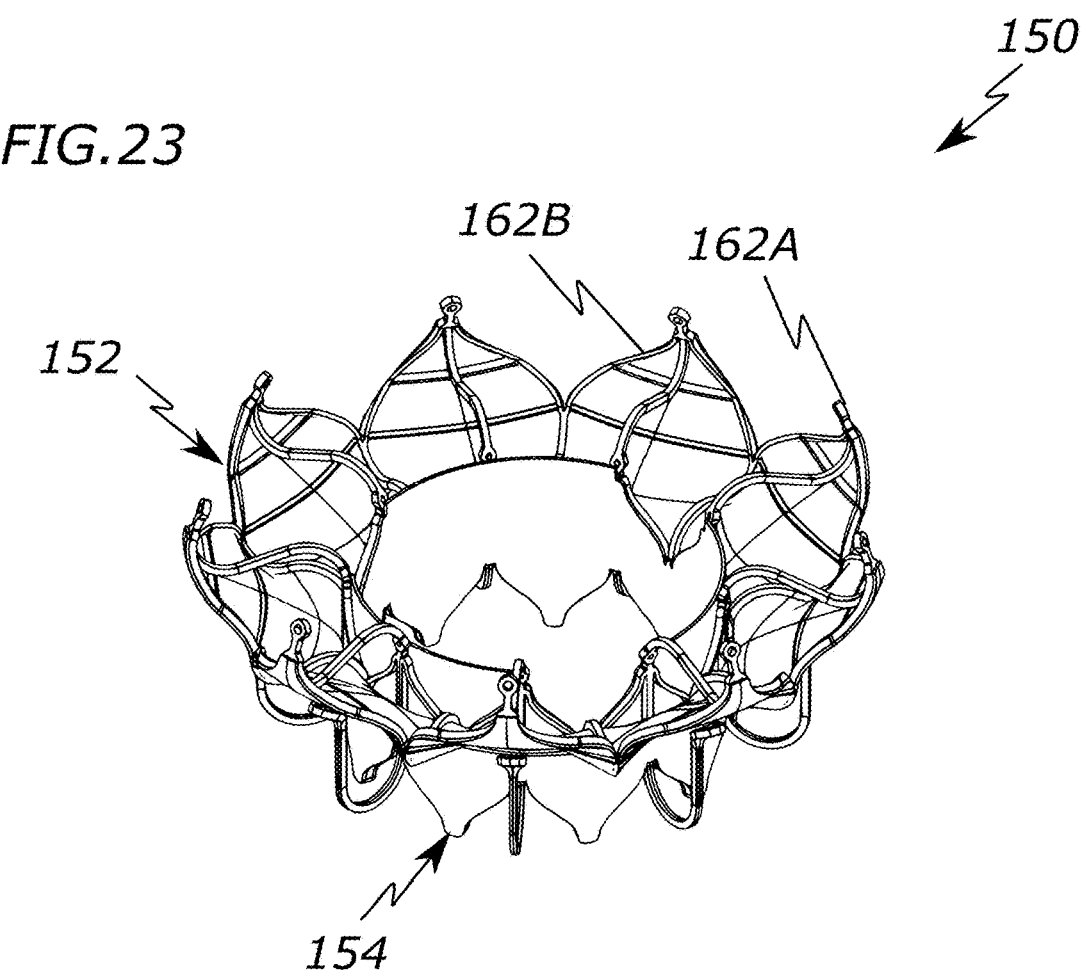
FIG. 23 is a perspective view of a prosthetic heart valve.
Figure 24:
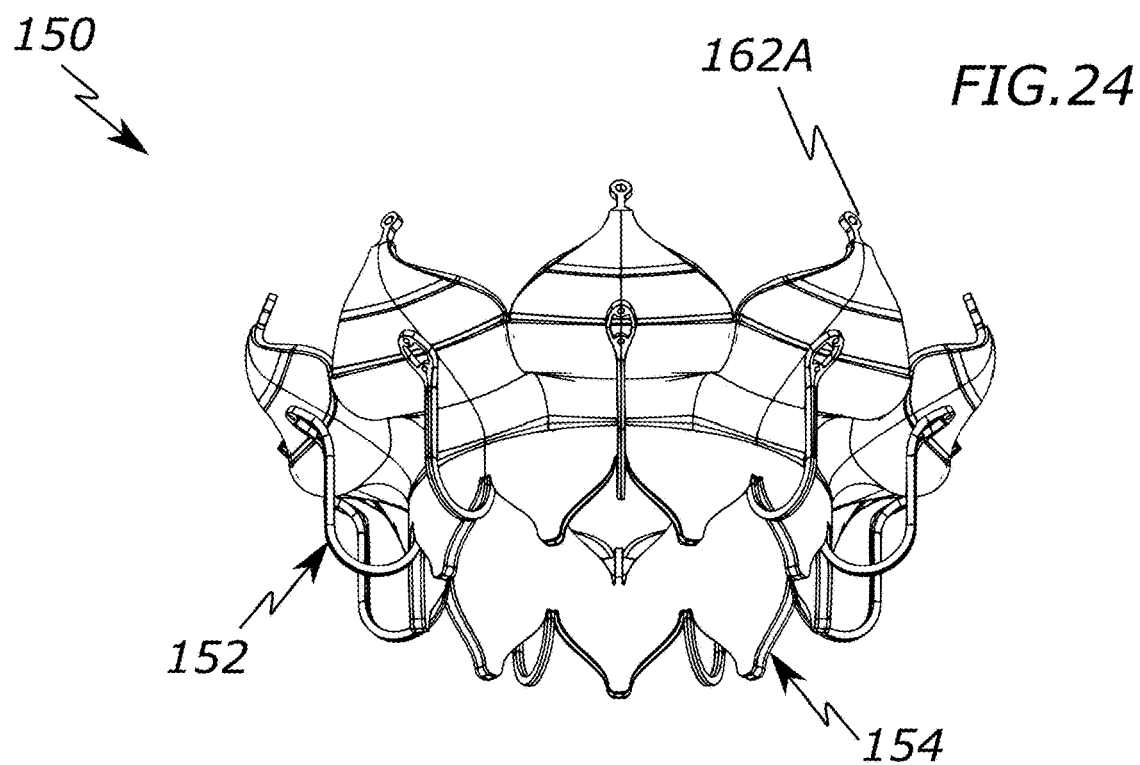
FIG. 24 is a view of the prosthetic heart valve of FIG. 23.
Figure 25:
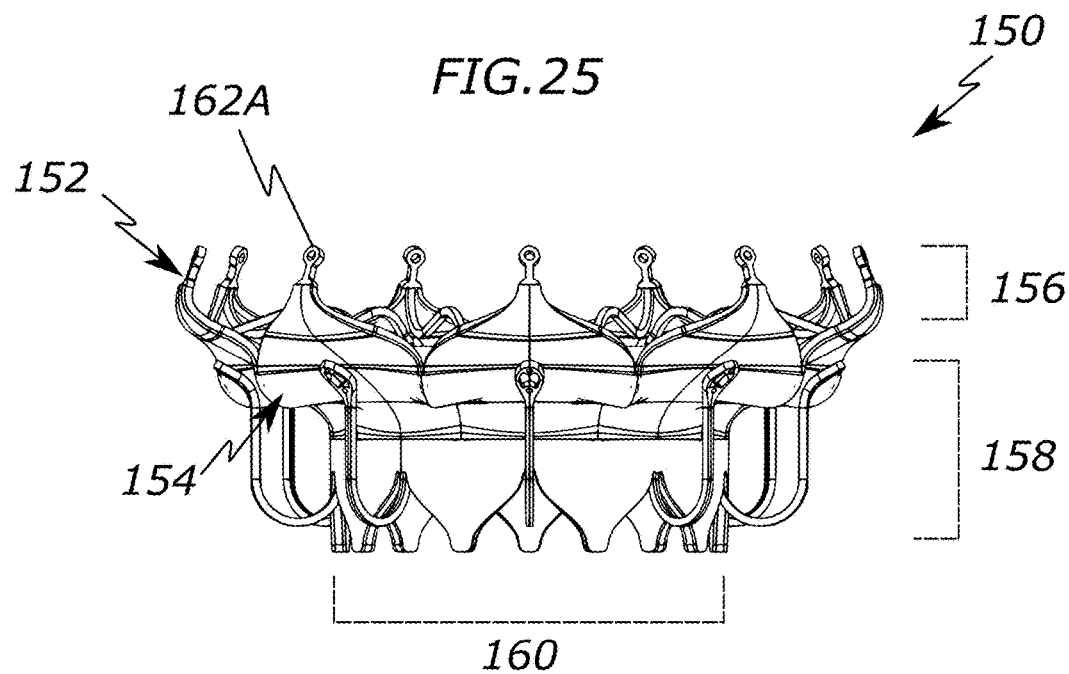
FIG. 25 is a side view of the prosthetic heart valve of FIG. 23.
Figure 26:
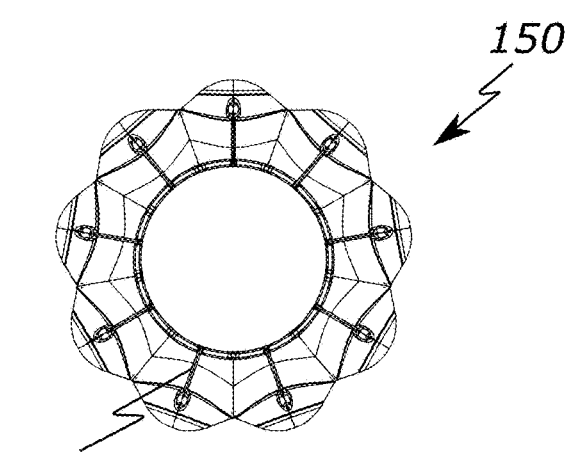
FIG. 26 is a bottom view of the prosthetic heart valve of FIG. 3.
Figure 27:
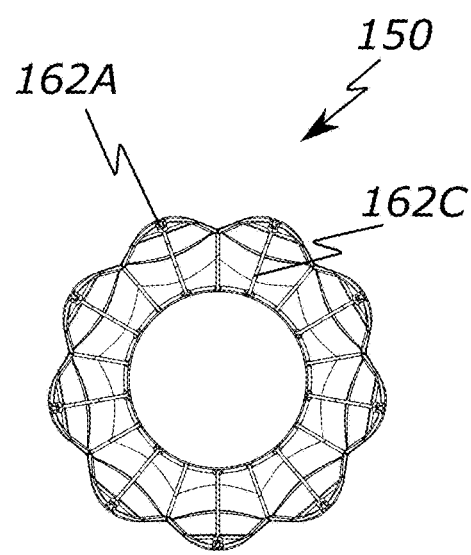
FIG. 27 is a top view of the prosthetic heart valve of FIG. 23.

In the present example, the leaflet engagement portion 158 may comprise a plurality of engagement struts 164 that are connected at an outflow end of the body portion 160 and extend in an inflow or upward direction. As will be described in further detail later, the engagement struts 164 curve generally parallel to the body portion 160 and then away from the body portion 160, terminating with an enlargement 164A (FIG. 23). The initial curve towards the body portion 160 may help engage or capture the native leaflets with the body portion 160. The enlargement 164A may be generally rounded to prevent damage to a patient's valve tissue and may further include one or more apertures that may be optionally used to releasably engage the support structure 150 by a delivery catheter 50.

In the present example, the engagement struts 164 are positioned at equal distances from each other around the circumference of the body portion 160. Again, non-uniform positioning of these struts 164 is also possible, such as only on opposite sides of the body portion 160 or in locations that may help avoid chordae within the ventricle.

The support structure 150 in the present example includes a rigid framework 152 and a material covering 154 that is disposed over portions of the framework 152. The material covering 154 is positioned over all or most of an inside and outside of the body portion 160 of the framework 152 (seen best in FIGS. 28 and 29), and over an outside of the atrial flange portion 156 of the framework 152. The engagement struts 164 are generally left uncovered by the material covering 154. As previously described, other variations are also possible, such as locating the material covering 154 on only the inside, only the outside, and/or on any combination of the portions 156, 158, 160.

Figure 28:
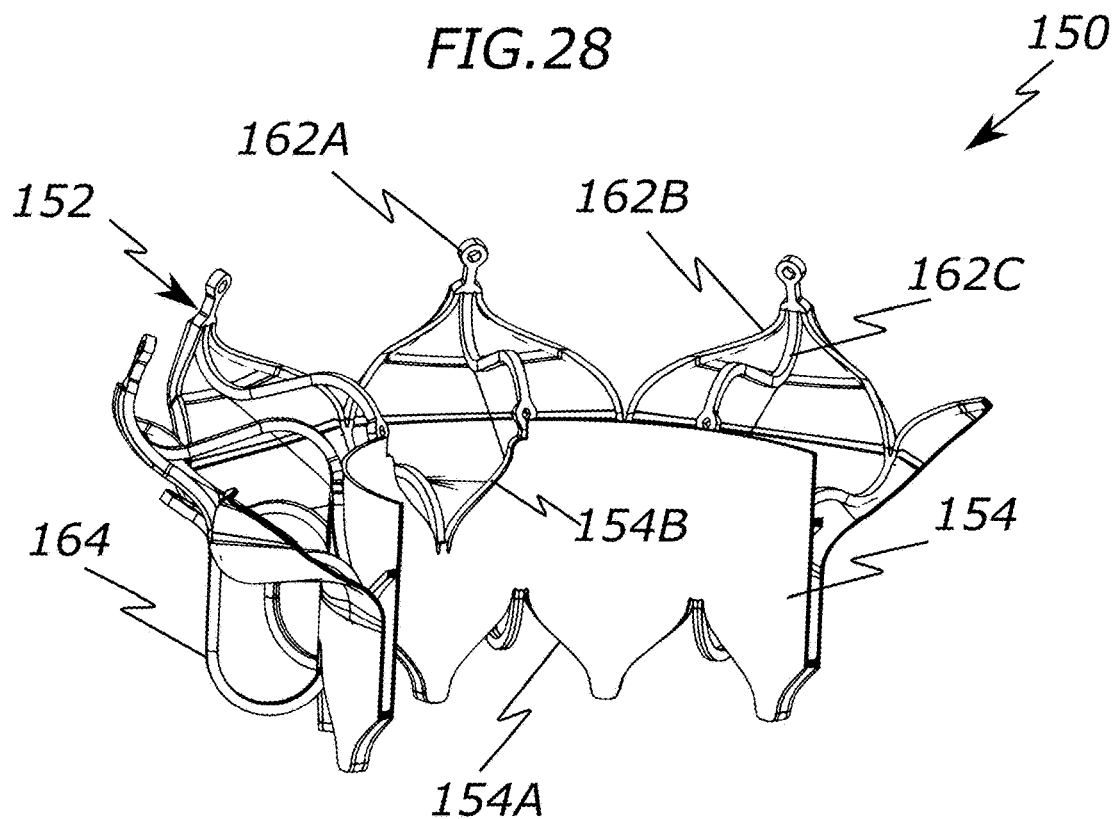
FIG. 28 is a cross-sectional view of the prosthetic heart valve of FIG. 23.
Figure 29:
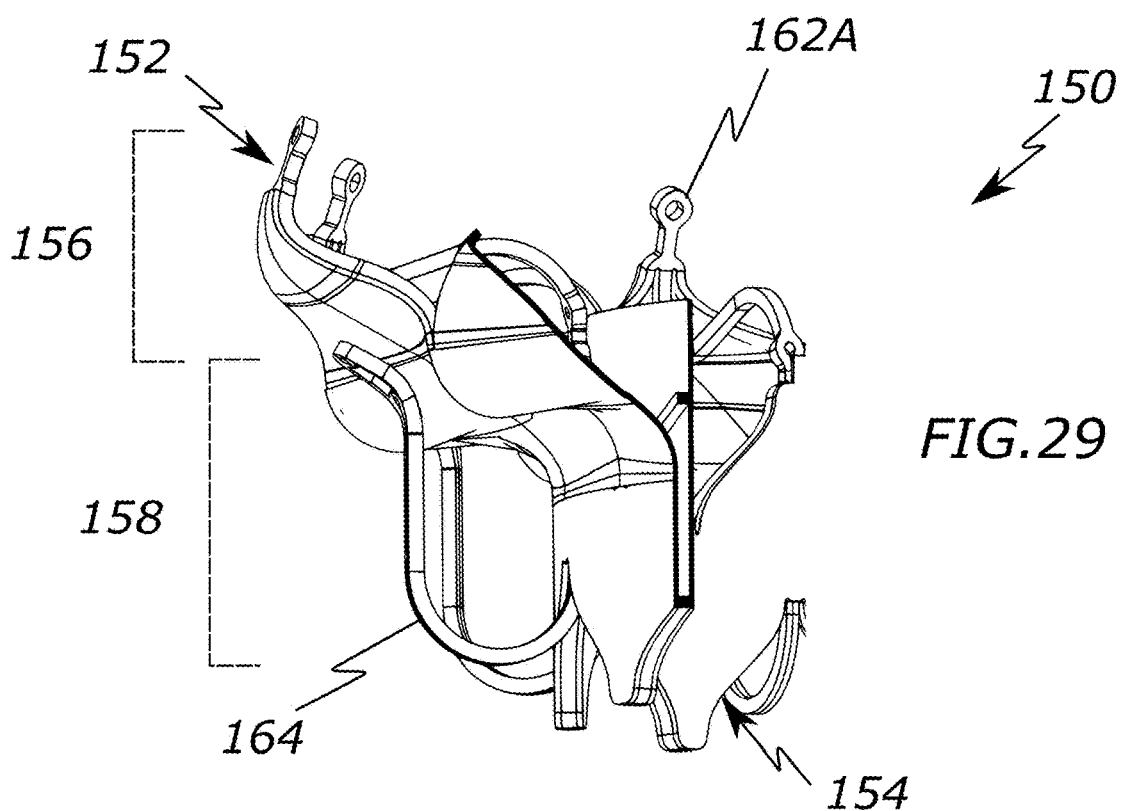
FIG. 29 is a cross-sectional view of the prosthetic heart valve of FIG. 23.
Figure 30:
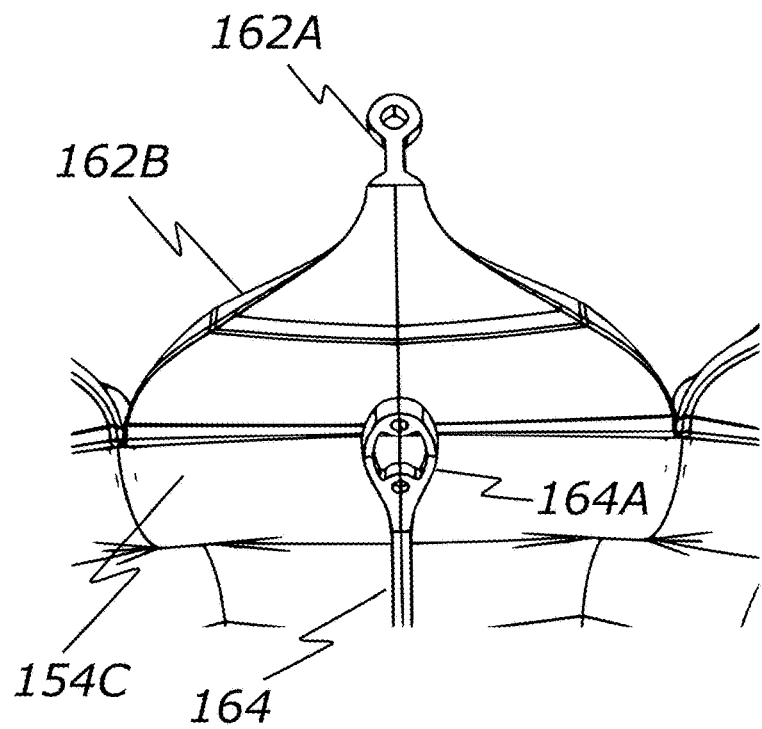
FIG. 30 is an enlarged view of the prosthetic heart valve of FIG. 23.
Figure 31:
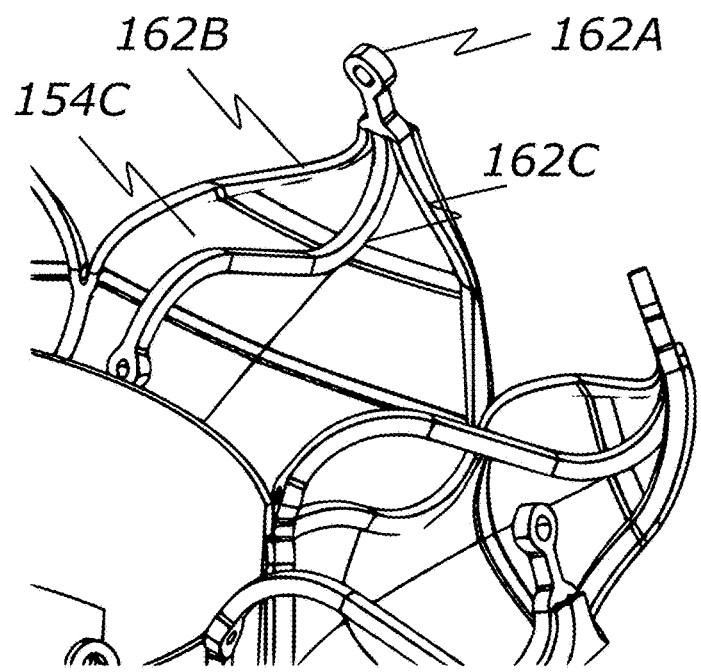
FIG. 31 is an enlarged view of the prosthetic heart valve of FIG. 23.
Figure 32:
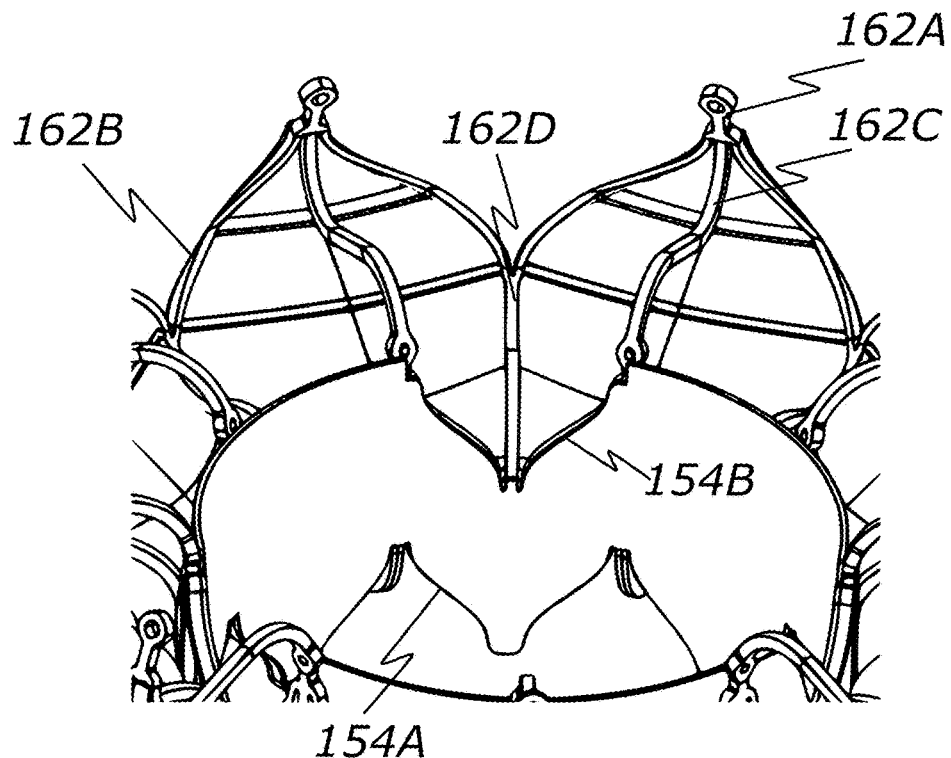
FIG. 32 is an enlarged view of the prosthetic heart valve of FIG. 23.

As best seen in FIGS. 28 and 29, the material covering 154 at the outflow end of the body portion 160 may form petals, pointed areas, or triangular areas 154A that generally match the underlying shapes of the framework 152 of the body portion 160. Alternatively, the outflow end of the body portion 160 may have a uniform circular-shaped edge.

Similarly, the edge of the material covering 154 at the inflow end of the body portion 160 may include one or more inset pointed or triangular gaps, spaces, or recesses 154B. While the triangular areas 154A are shown immediately adjacent to each other, the recesses 154B may be less frequent between relatively uniform edge regions. However, the inflow edge or outflow edge may take on either of the disclosed patterns in any combination, as well as have a completely uniform and perpendicular edge. As also seen in FIG. 23, the material covering 154C may also conform to the shape of the triangles or pointed petal shape of the atrial flange portion 156.

In the present example, the material covering 154 may be attached by adhesive, stitches, combinations thereof, and similar mechanisms. The material covering 154 may be composed of textile material, EPTFE sheets, PET sheets, and similar materials discussed elsewhere in this specification. In addition to the material covering 154, additional materials may be included on an underside of the atrial flange portion 156 to help create a better seal with the native valve annulus, such as hydrogel.

FIGS. 34-44 illustrate various aspects of the framework 152 in the present example. The body portion 160 of the framework 152 is composed of a plurality of elongated vertical body struts 166B and a plurality of horizontal body struts 166A (best seen in the cross-sectional view of FIG. 37). The vertical body struts 166B are generally parallel to an axis through the support structure's passage (i.e., an axis from the inflow end to the outflow end), while the horizontal body struts 166A are positioned around this axis in a circular shape.

The vertical body struts 166B may alternate between different heights or axial positions, such that a first vertical body strut 166B has a first axial position and the two vertical body struts 166B adjacent to the first is positioned further in an inflow direction relative to the adjacent two. Hence, the vertical body struts 166B may form an alternating pattern.

The horizontal body struts 166A may form a "V" shape or a relatively sharp angle pointing towards the outflow direction, though the opposite direction is also possible. Each end of a horizontal body strut 166A connects to a vertical body strut 166B, as well as a vertical body strut 166B passes directly through the middle of the "V" shape. The "V" shape of the horizontal body strut 166A provides a bend point at the apex of its "V" to increase and decrease its angle depending on whether the support structure 150 is in its compressed configuration or expanded configuration. In other words, the "V" shape facilitates this radial compression and expansion. Alternatively, other shapes with angles in them may also be possible for the horizontal body structure 166A, such as a "W" shape with two or more angles. In the present example, there are two rows of horizontal body struts 166A, though more rows are possible.

In one example, the body portion 160 of the framework 152 has a length within an inclusive range of about 14 mm to about 18 mm, and has a radius within an inclusive range of about 27 mm to about 30 mm.

The atrial flange portion 156 of the framework 152 includes a plurality of flange struts 162. The shape of these flange struts 162 can be best seen in FIGS. 38-46. The atrial flange portion 156 alternates with an upper radial strut 162C and a lower radial strut 162D. Both struts 162C, 162D each extend from a vertical body strut 166B. While both struts 162C, 162D may have similar shapes/size/curvature, the upper radial struts 162C are generally higher (i.e., further in an inflow direction) than lower radial struts 162D, due to the higher and lower positions of the vertical body struts 166B (e.g., due to the "V" shape/position of the horizontal body struts 166A). In the present example, an aperture portion 166C is located adjacent to the vertical body strut 166A and the upper radial strut 162. This aperture portion 166C may be optionally included for use with a delivery catheter 50.

Figure 33:
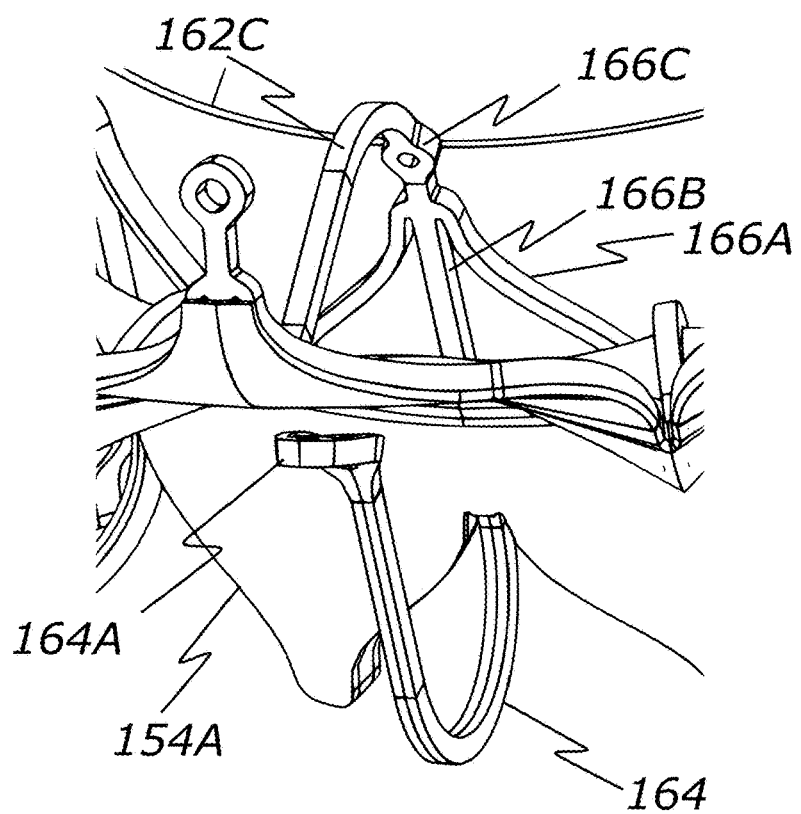
FIG. 33 is an enlarged view of the prosthetic heart valve of FIG. 23.
Figure 34:
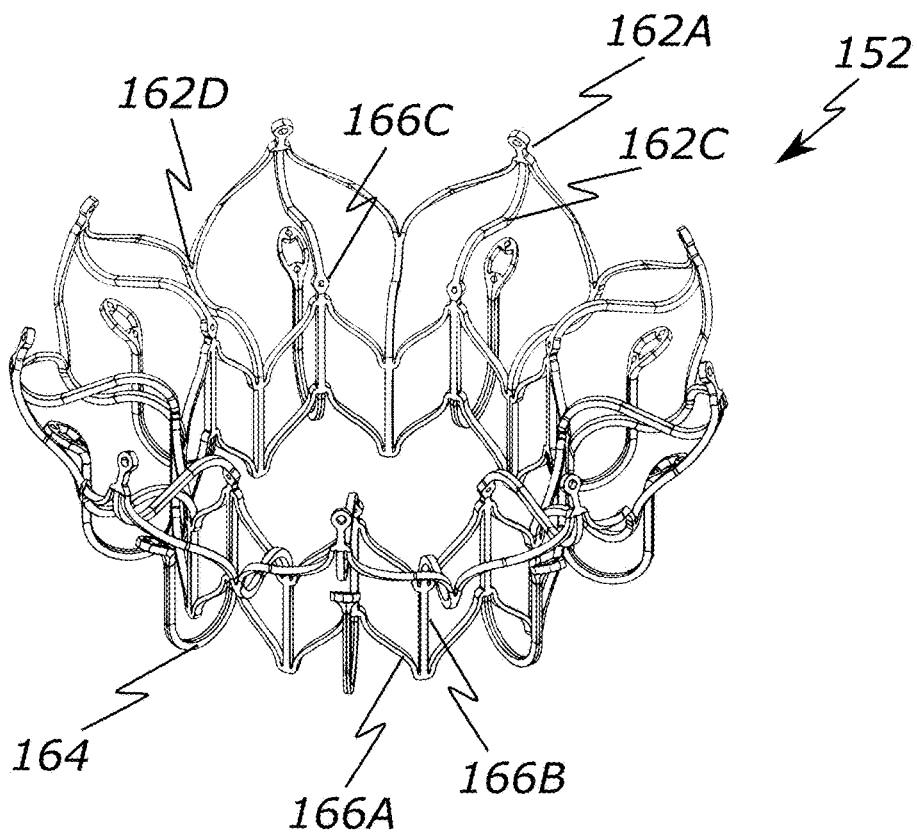
FIG. 34 is a perspective view of a framework of the prosthetic heart valve of FIG. 23.
Figure 35:
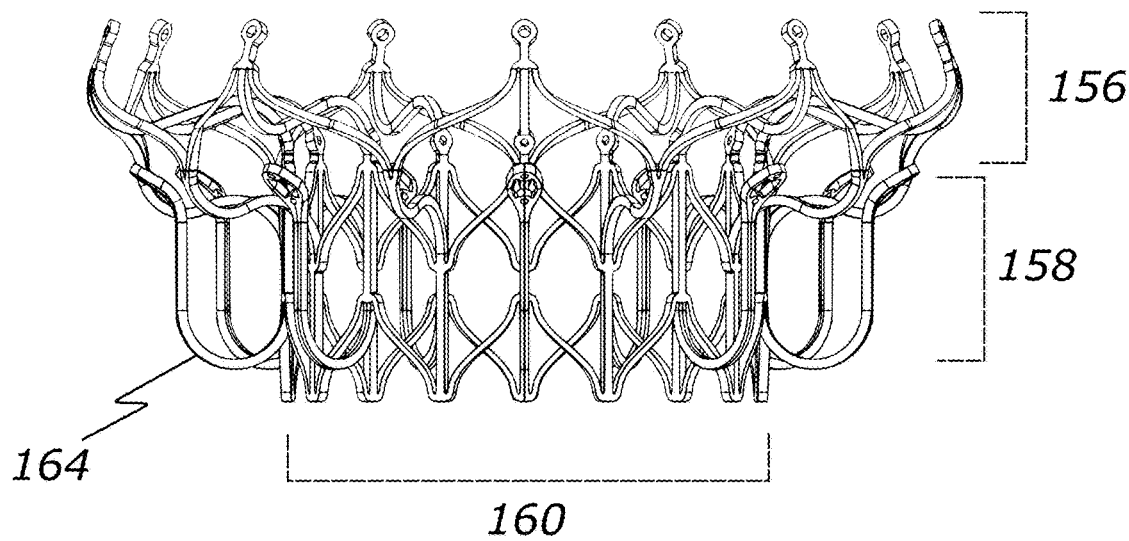
FIG. 35 is a side view of a framework of the prosthetic heart valve of FIG. 23.
Figure 36:
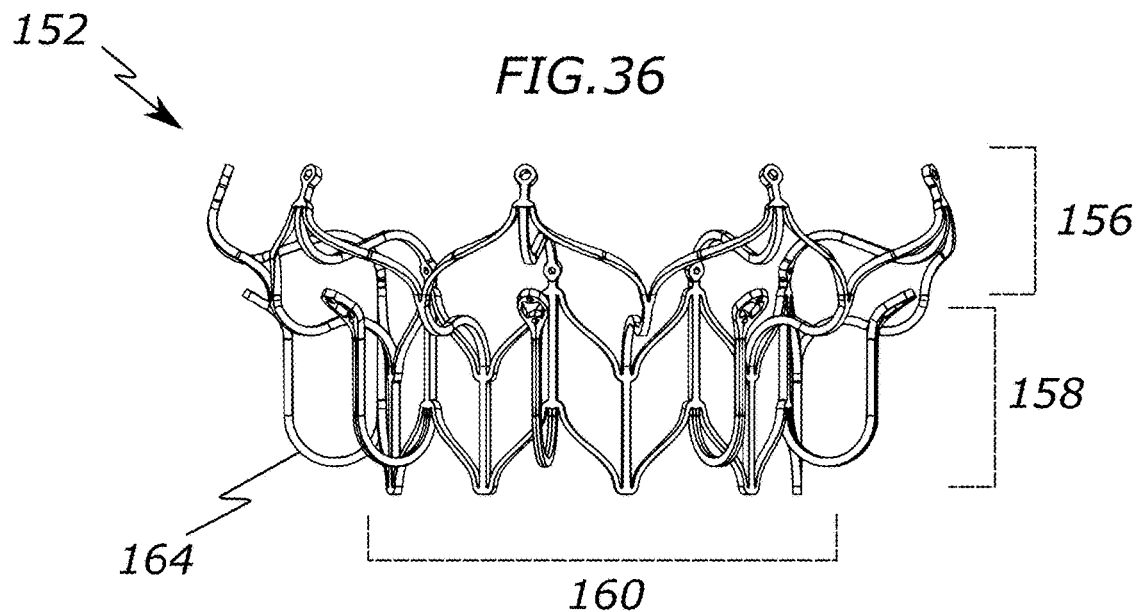
FIG. 36 is a side view of a framework of the prosthetic heart valve of FIG. 23.
Figure 37:
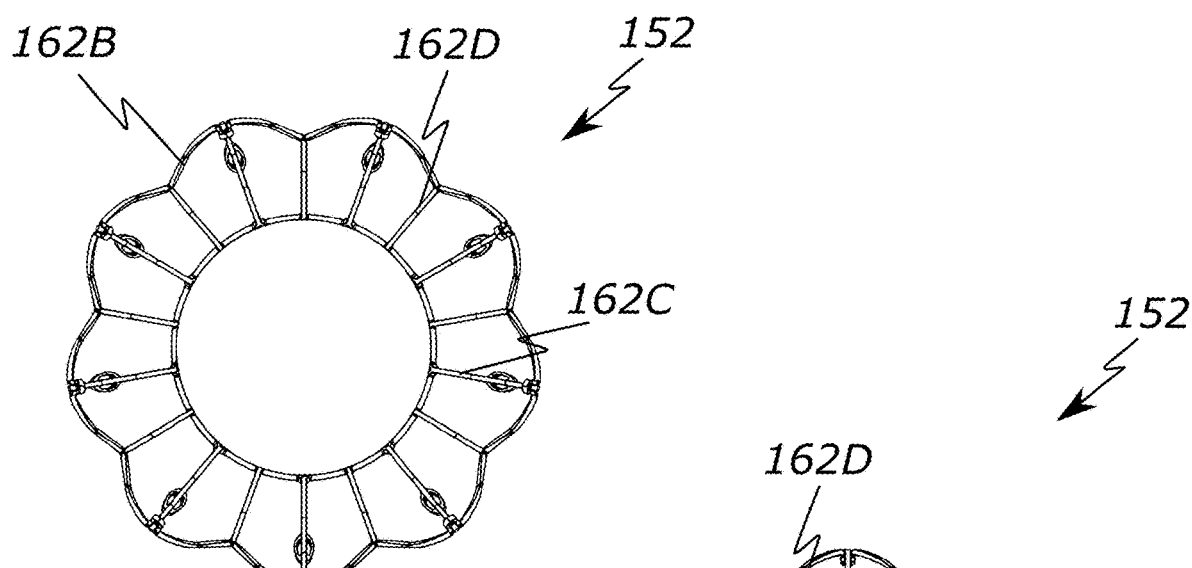
FIG. 37 is a top view of a framework of the prosthetic heart valve of FIG. 3.
Figure 38:
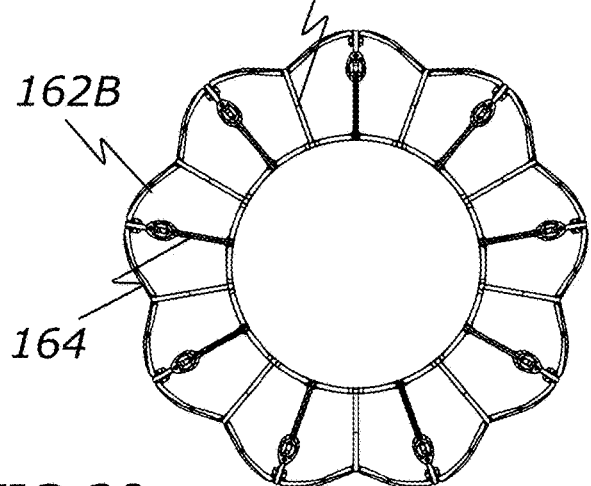
FIG. 38 is a bottom view of a framework of the prosthetic heart valve of FIG. 23.

As seen in FIG. 33, each upper radial flange strut 162C forms a first angle 162E within an inclusive range of about 90 degrees and 130 degrees, a relative straight portion 162F with a length within an inclusive range of about 3 mm and about 10 mm, a second angle 162G within an inclusive range of about 20 degrees and about 150 degrees, and a terminal portion 162A with a length within an inclusive range of about 1 mm and 7 mm (again, angles relative to an inflow/outflow oriented axis of the support structure 150). Generally, the specific angles and sizes may vary somewhat depending on the heart and valve size of the patient. The terminal portion 162A may optionally include an aperture that can be used by a delivery catheter 50 to help releasably retain the support structure 150 during deployment.

As seen in FIG. 40, each lower radial flange strut 162D forms a first angle 162H within an inclusive range of about 90 degrees and 150 degrees, a relative straight portion 162I with a length within an inclusive range of about 0 mm and about 5 mm, a second angle 162J within an inclusive range of about 0 degrees and about 60 degrees, and a terminal portion 162K with a length within an inclusive range of about 1 mm and 7 mm (again, angles relative to an inflow/outflow oriented axis of the support structure 150). Generally, the specific angles and sizes may vary somewhat depending on the heart and valve size of the patient. The terminal portion 162K may optionally include an aperture that can be used by a delivery catheter 50 to help releasably retain the support structure 150 during deployment.

The radially outer ends of each upper radial strut 162C and lower radial strut 162D are connected to each other via one of a plurality of circumferential radial struts 162B. Since the upper radial strut 162C and lower radial strut 162D are located at different heights and distances from each other, the circumferential radial struts 162B tend to form relatively triangular or petal shapes that terminate with terminal portion 162A. Hence, the circumferential radial struts 162B may curve in several dimensions to accommodate the upper radial strut 162C and lower radial strut 162D position difference.

The leaflet engaging portion 158 of the framework 152 includes a plurality of engagement struts 164, the shape of which can be best seen best in FIG. 39. Generally the engagement struts 164 have a straight portion 164B that is parallel to an axis through the support structure's passage (i.e., an axis from the inflow end to the outflow end). In other words, the engagement strut 164 does not angle towards the body portion 160 like the prior support structure 100, though such a configuration is possible. The engaging struts 164 are connected to the outflow end of the vertical body struts 166B. From the vertical body strut 166B, the engagement strut 164 forms a first curve 164C which curves around to about 180 degrees (e.g., an inclusive range of about 150 degrees to about 230 degrees), a first straight portion 164B with a length within an inclusive range of about 3 mm and about 10 mm, a second curve 164D curving in an opposite direction of curve 164C within an inclusive range of about 90 degrees to about 150 degrees, and a rounded portion 164A with a length within an inclusive range of about 2 mm to about 10 mm. While these curves all generally occur in the same plane, it is possible to include additional curves that may take some of the engagement struts 114 out of a single plane (i.e., curving in multiple dimensions). The rounded portion 164A may optionally include an aperture that may be used by the delivery catheter 50 to releasably retain the support structure 150 during deployment.

As previously discussed, the engagement struts 164 are not covered by the material covering 154 in the present example, but may be. Additionally, the engagement struts 164 may be coated or wrapped in a relatively softer material (e.g., a textile or EPTFE layer). Further, the rounded portion 164A of the engagement struts 164 may include a coating composed of similar materials or other materials described in this specification.

Figure 45:
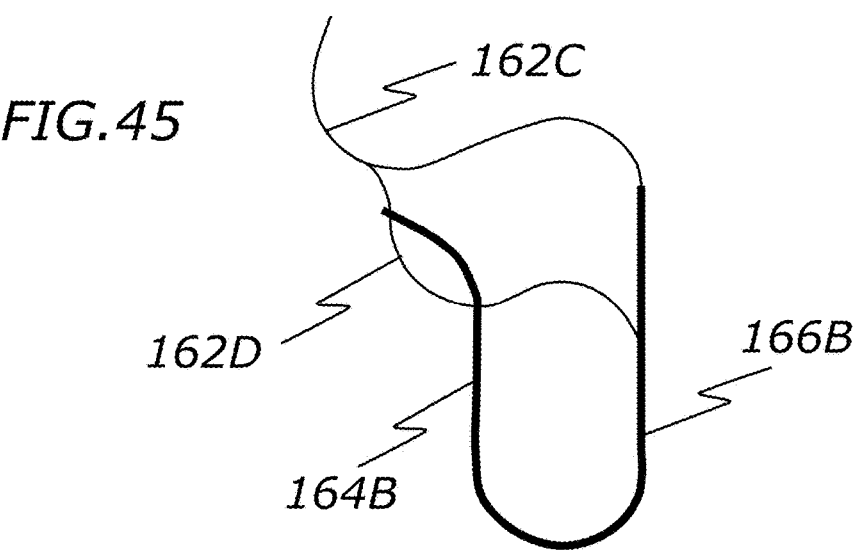
FIG. 45 is a simplified line view of several components of the prosthetic heart valve of FIG. 23.

One aspect of the support structure 150 and framework 152 of note is the positions of the atrial flange 156 relative to the engagement struts 164, as seen best in the simplified line view of FIG. 45, as well as FIG. 39. In its expanded configuration, the end portions of the engagement struts 164 (i.e., portions of the leaflet engaging portion) are positioned at a more proximal location or further in an inflow direction than portions the radially-adjacent lower radial struts 162D of the atrial flange portion 156. In other words, lower radial struts 162D on each side of each of the engagement struts 164 curve axially in a distal/outflow direction beyond the end portion of the engagement struts 164. In one example, the axially-adjacent overlap is within an inclusive range of about 0.1 mm to about 10 mm.

This arrangement may be particularly helpful in several respects. First, this arrangement forces the leaflets and the annulus of the native valve to be positioned over the engagement struts 164 and then below the lower radial struts 162D, forcing the leaflets/annulus into an alternating or wave-like shape. Hence, the leaflet engaging portion 158 (i.e., engagement struts 164) and the atrial flange portion 156 (i.e., lower radial struts 162D) tend to pinch the leaflets/annulus and create a paperclip effect. This design may allow for positive remodeling (e.g., size reduction of any enlargement) of the ventricle as the body adapts to the reduced regurgitation vs the prior faulty native valve. Some other prosthetic replacement valves may be relatively large plug-like designs and may rely on radial force to anchor and seal, but the present top-down approach to sealing at the annulus may allow the ventricle to better recover over time and reduce in diameter without interference from the present replacement valve.

Second, this arrangement may hold the material covering on the underside of the atrial flange portion taut around the top of the leaflet engaging portion so that there is good contact between the material covering and the leaflets/annulus to promote sealing, healing, and possibly tissue in-growth.

Third, portions of the lower radial struts 162D (e.g., those closes to the outflow end of the framework 152, such as 162H) may be positioned within the annulus of the native valve. Since portions of the lower radial struts 162D may curve radially outward, this shape may help further seal the framework 152 with the native annulus, further limiting the passage of blood around the framework/valve.

The framework 152 of the present example may be composed of a single unitary body, such as laser cut from a shape memory tube (e.g., Nitinol tube). Alternatively, one or more of the struts of the framework may be welded or otherwise attached to each other. Alternatively, some of the components may be separate from each other, only connected by other materials, such as the material covering 154 or other attachment mechanisms. For example, the body portion 160, the leaflet engagement portion 158, and/or the atrial flange portion 156 may not be directly attached to each other in any combination. If shape memory material is used for the framework 152, the framework may be cut to a desired pattern and then heat set to impart a desired shape in its expanded configuration.

Figure 47:
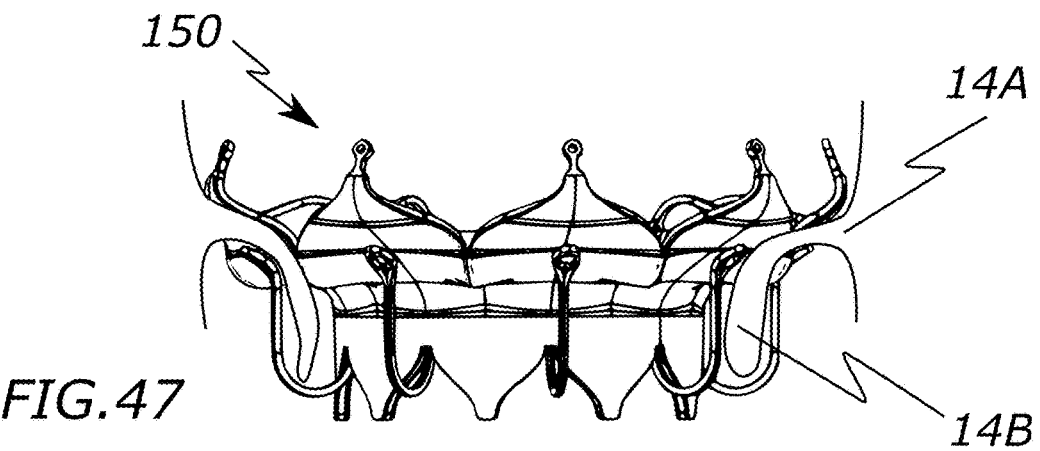
FIG. 47 is a side view of the prosthetic heart valve of FIG. 23 in a native heart valve.

The support structure 150 may deploy from a delivery catheter 50 in the same manner as described for the support structure 100 in FIGS. 10-12. In that respect, the engagement struts 164 may begin in a compressed configuration with their ends (rounded enlargement 164A) positioned distally away from the body portion 160 within the delivery catheter 50. As the support structure 150 is pushed out or an outer sheath is retracted from over the support structure 150, the engagement struts 164 extend radially outward from the delivery catheter 50, and then, as the support structure 150 continues to advance or be exposed, the engagement struts 164 bend backward such that the rounded enlarged end 164A is positioned in an inflow direction relative to the outflow end of the body portion 160. In other words, as deployment occurs, the engagement struts 164 bend radially backward or invert which allows them to capture the native valve leaflets 14B with the body portion 160 and press against the valve annulus, as seen in FIG. 47.

In a compressed configuration within the delivery catheter 50, it should be noted that the terminal portion 162A with an aperture may be located at a proximal end of the compressed support structure 150 while engagement struts 164 are constrained distally such that the rounded portion 164A is at a distal most location within the delivery device 50. In that respect, apertures are located at both the proximal and distal ends of the support structure 150 in its compressed configuration. Additionally, aperture portion 166C also includes an aperture midway along the length of the compressed configuration. These apertures may be engaged with features of the delivery device 50, such as posts, hooks, tethers, or similar structures that help retain portions of the support structure until 150 until fully deployed.

Figure 46:
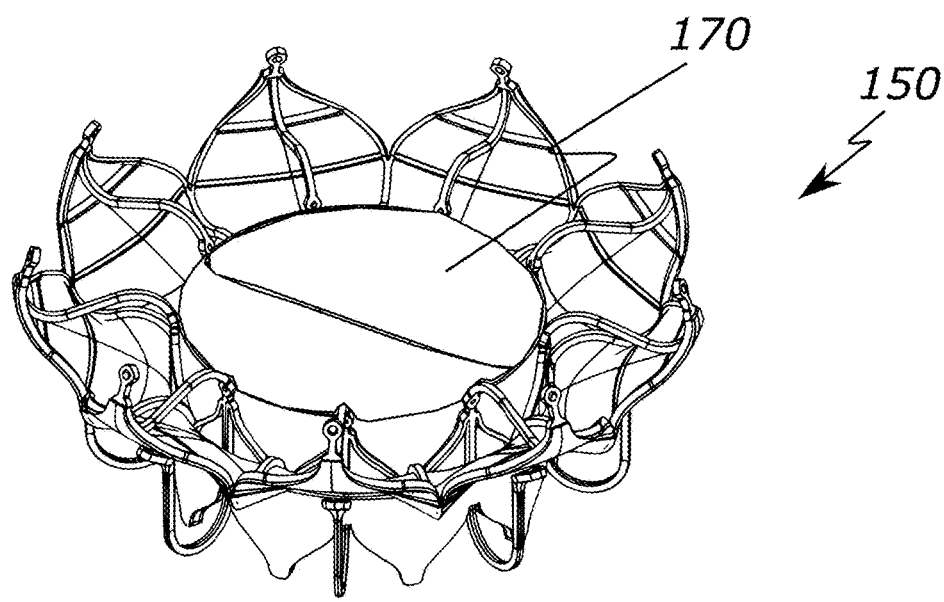
FIG. 46 is a view of the prosthetic heart valve of FIG. 23 with valve leaflets.

As previously discussed, although the support structure 100 and 150 are mostly described in this specification, it is specifically contemplated that a valve mechanism 170, such as prosthetic or biological valve leaflets, be attached within the valve support mechanism, as seen in FIG. 46.

Figure 48:
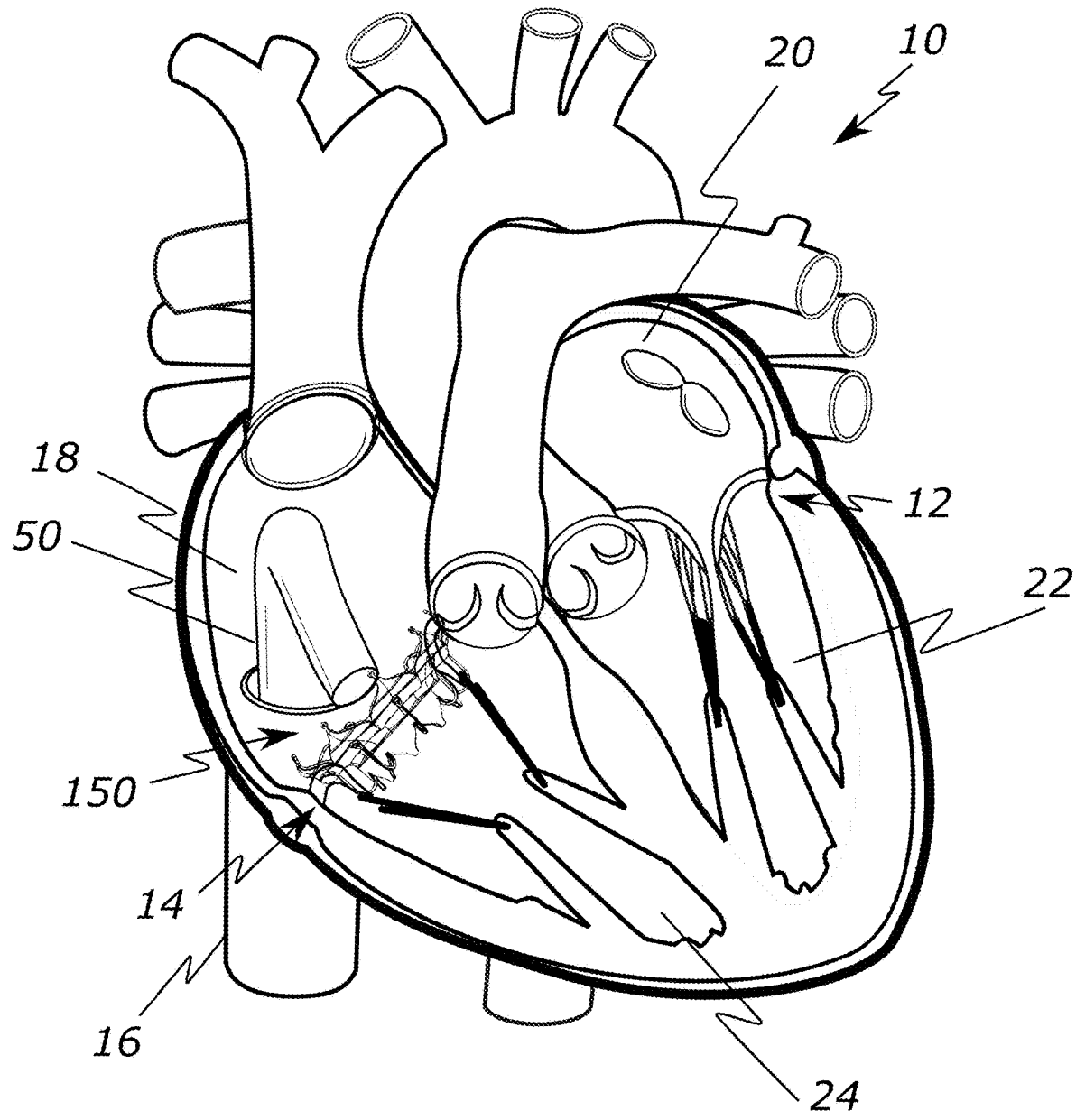
FIG. 48 is a side view of the prosthetic heart valve of 3. 23 in a native heart valve.

FIG. 48 illustrates one approach to delivering a support structure 150 within a tricuspid valve 14 by advancing a delivery catheter through the inferior vena cava 16 and into the right atrium 18, such that the support structure 150 is delivered from an inflow or atrial end relative to the tricuspid valve 14.

Figure 49:
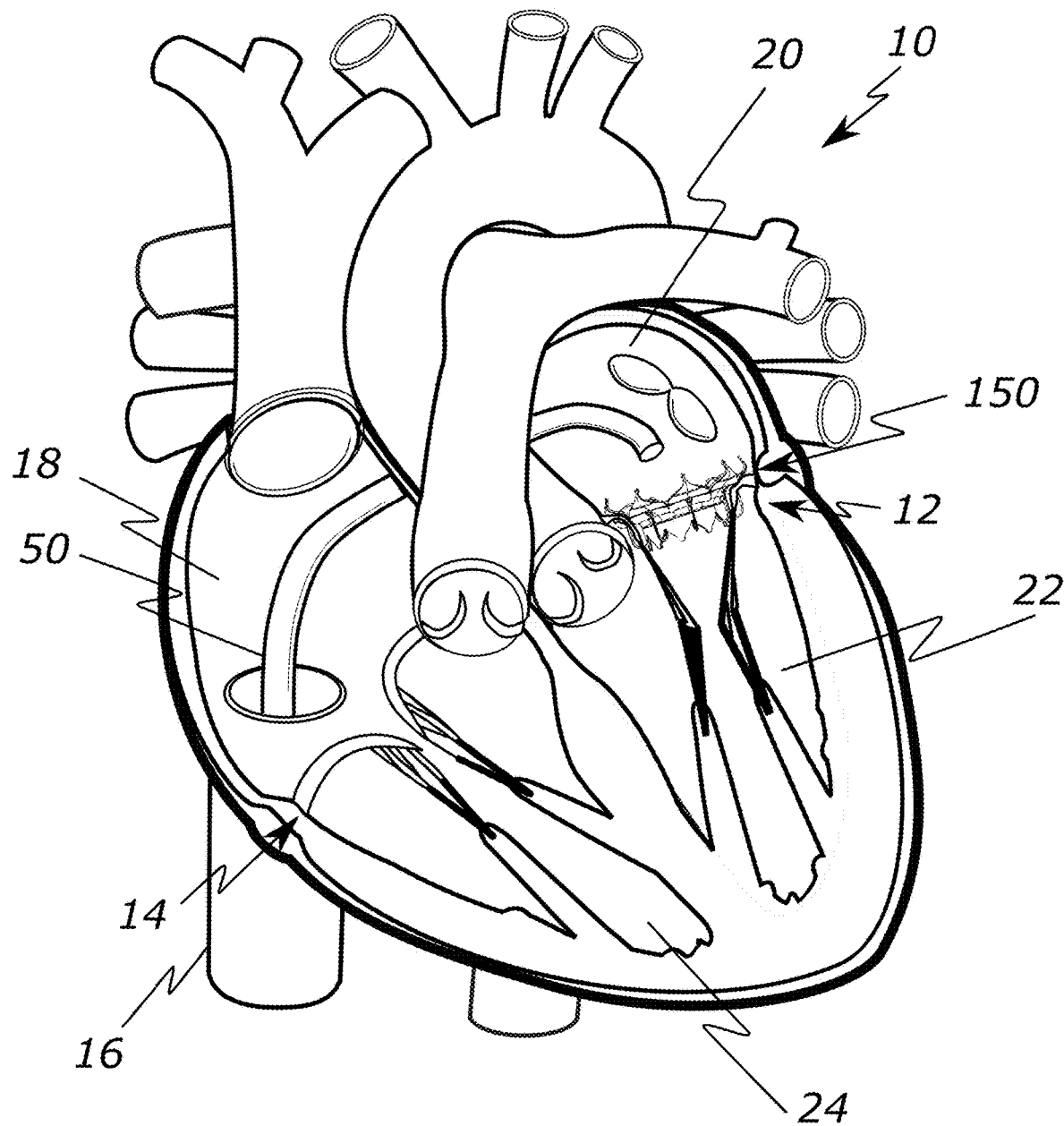
FIG. 49 is a side view of the prosthetic heart valve of FIG. 23 in a native heart valve.

FIG. 49 illustrates another approach to delivering a support structure 150 with a mitral valve 12 by performing a transseptal procedure to allow the delivery catheter to pass through the septum between the right atrium 18 and the left atrium 20. This allows the support structure 150 to be delivered from an inflow or atrial end relative to the mitral valve 12.

Additional approaches to delivering the support structure 150 are also possible. For example, either valve 14, 20 may be approached from its respective ventricle. In such cases, the support structure may be arranged in an opposite orientation as shown in FIGS. 10-12.

Any of the support structures in this specification, including support structures 100 and 150, may be delivered from one of several known heart valve delivery devices. For example, the devices in U.S. Pub. No. 2017/0165064, 2019/0008640, and 2022/0287836, the content of which is hereby incorporated by reference.

Although the invention has been described in terms of particular embodiments and applications, one of ordinary skill in the art, in light of this teaching, can generate additional embodiments and modifications without departing from the spirit of or exceeding the scope of the claimed invention. Accordingly, it is to be understood that the drawings and descriptions herein are proffered by way of example to facilitate comprehension of the invention and should not be construed to limit the scope thereof.

What is claimed is:

1. A framework for a prosthetic heart valve having an expanded configuration comprising:
a body portion having a passage extending longitudinally between an inflow end positioned in an inflow direction and an outflow end positioned in an outflow direction;
a plurality of atrial flange struts connected at and extending radially outward from the inflow end of the body portion so as to contact an inflow side of a native valve annulus; the plurality of atrial flange struts forming an alternating pattern between some struts in an upper position and some struts in a lower position around the body portion and relative to the inflow end; and,
a plurality of engagement struts connected near the outflow end of the body portion and positioned along an outer side of the body portion toward the inflow direction; wherein regions of the plurality of engagement struts are located longitudinally beyond at least a portion of some of the atrial flange struts in the inflow direction.

2. The framework of claim 1, wherein the plurality of engagement struts are also located radially closer to the body portion than some regions of the atrial flange struts.

3. The framework of claim 1, wherein the plurality of engagement struts are each entirely also located radially closer to the body portion than some regions of the atrial flange struts.

4. The framework of claim 1, wherein the regions of the plurality of engagement struts are located longitudinally beyond at least the portion of some of the atrial flange struts in the direction of the inflow end of the body portion by a distance within an inclusive range of about 0.1 mm to about 10 mm.

5. The framework of claim 1, wherein each of the plurality of engagement struts are positioned radially between two of the plurality of atrial flange struts in the lower positions around the body portion, such that when positioned in the native valve, the annulus of the native valve forms an alternating wave-like shape.

6. The framework of claim 1, wherein the plurality of engagement struts comprise a straight portion that is parallel to an axis through the passage of the body portion.

7. The framework of claim 1, wherein the plurality of engagement struts comprise a first curve attached near the outflow end of the body portion and that curves at about 180 degrees; a straight portion connected to the first curve and that is parallel to an axis through the passage of the body portion, and a second curve that curves in an opposite direction of the first curve.

8. The framework of claim 1, wherein end portions of the plurality of atrial flange struts in the upper position are located further radially outward from the body portion than end portions of the atrial flange struts in the lower position.

9. The framework of claim 1, further comprising a prosthetic valve mechanism comprising prosthetic valve leaflets; wherein the prosthetic valve mechanism is attachable to the framework.

10. The framework of claim 1, further comprising a prosthetic valve mechanism comprising prosthetic valve leaflets; wherein the prosthetic valve mechanism is attached to the framework.

11. The framework of claim 1, further comprising a material covering forming a first plurality of triangular petal shapes over the plurality of atrial flange struts.

12. The framework of claim 11, wherein the material covering forms a second plurality of triangular petal shapes near the outflow end of the body portion; and wherein the plurality of engagement struts are positioned between each of the second plurality of triangular petal shapes.

13. The framework of claim 1, wherein a terminal portion of the plurality of atrial flange struts each comprise an atrial aperture and wherein a terminal portion of the plurality of engagement struts each comprise an engagement aperture, wherein the atrial aperture and the engagement aperture are each releasably connected to a delivery device.

14. A framework for a prosthetic heart valve having an expanded configuration comprising:
   a body portion having a passage extending between an inflow end positioned in an inflow direction and an outflow end positioned in an outflow direction;
   a plurality of upper atrial flange struts connected at and extending radially outward from the inflow end of the body portion to contact an inflow side of a native valve annulus, and a plurality of lower atrial flange struts connected at and extending radially outward from the inflow end of the body portion to contact an inflow side of the native valve annulus; wherein the upper atrial flange struts are positioned further in the inflow direction than the plurality of lower atrial flange struts; and wherein the upper atrial flange struts and the lower atrial flange struts form an alternating pattern around the body portion; and,
   a plurality of engagement struts connected near the outflow end of the body portion and positioned along an outer side of the body portion in the inflow direction; wherein end regions of the plurality of engagement struts are positioned beyond at least a portion of the lower atrial flange struts in the inflow direction.

15. The framework of claim 14, wherein the plurality of engagement struts are also located entirely radially closer to the body portion than some regions of the upper atrial flange struts and the lower atrial flange struts.

16. The framework of claim 15, wherein the end regions of the plurality of engagement struts are located longitudinally beyond at least the portion of the lower atrial flange struts in the direction of the inflow end of the body portion by a distance within an inclusive range of about 0.1 mm to about 10 mm.

17. The framework of claim 16, wherein each of the plurality of engagement struts are positioned radially between two of the plurality of lower atrial flange struts around the body portion, such that when positioned in a native valve, an annulus of the native valve forms an alternating wave-like shape.

18. The framework of claim 17, wherein the plurality of engagement struts comprise a first curve attached near the outflow end of the body portion and that curves at about 180 degrees; a straight portion connected to the first curve and that is parallel to an axis through the passage of the body portion, and a second curve that curves in an opposite direction of the first curve.

19. The framework of claim 18, wherein end portions of the plurality of upper atrial flange struts are located further radially outward from the body portion than end portions of the lower atrial flange struts.

20. A framework for a prosthetic heart valve having an expanded configuration comprising:
   a body portion having a passage extending between an inflow end positioned in an inflow direction and an outflow end positioned in an outflow direction;
   a plurality of upper atrial flange struts connected at and extending radially outward from the inflow end of the body portion, and a plurality of lower atrial flange struts connected at and extending radially outward from near the inflow end of the body portion; wherein the upper atrial flange struts are positioned closer to the inflow end of the body portion than the plurality of lower atrial flange struts; and wherein the upper atrial flange struts and the lower atrial flange struts form an alternating pattern around the body portion; and,
   a plurality of engagement struts connected near the outflow end of the body portion and positioned along an outer side of the body portion toward the inflow direction; wherein regions of the plurality of engagement struts are longitudinally-positioned between at least a portion of each of the plurality of lower atrial flange struts and a portion of each of the plurality of upper atrial flange struts; and wherein the regions of the plurality of engagement struts are also radially-positioned between the body portion and the plurality of lower atrial flange struts.

* * * * *